United States Patent
Ogembo et al.

(10) Patent No.: US 12,156,911 B2
(45) Date of Patent: Dec. 3, 2024

(54) MULTIVALENT KAPOSI SARCOMA-ASSOCIATED HERPESVIRUS-LIKE PARTICLES AND USES THEREOF

(71) Applicant: CITY OF HOPE, Duarte, CA (US)

(72) Inventors: Javier Gordon Ogembo, Duarte, CA (US); Lorraine Zvichapera Mutsvunguma, Duarte, CA (US); David H. Mulama, Duarte, CA (US); Murali Muniraju, Duarte, CA (US); Felix Wussow, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 458 days.

(21) Appl. No.: 17/431,856

(22) PCT Filed: Feb. 21, 2020

(86) PCT No.: PCT/US2020/019207
§ 371 (c)(1),
(2) Date: Aug. 18, 2021

(87) PCT Pub. No.: WO2020/172522
PCT Pub. Date: Aug. 27, 2020

(65) Prior Publication Data
US 2022/0143174 A1    May 12, 2022

Related U.S. Application Data

(60) Provisional application No. 62/809,481, filed on Feb. 22, 2019.

(51) Int. Cl.
| | |
|---|---|
| *A61K 39/245* | (2006.01) |
| *A61K 39/00* | (2006.01) |
| *A61K 39/17* | (2006.01) |
| *A61P 31/22* | (2006.01) |
| *C07K 14/005* | (2006.01) |

(52) U.S. Cl.
CPC ............ *A61K 39/245* (2013.01); *A61K 39/17* (2013.01); *A61P 31/22* (2018.01); *C07K 14/005* (2013.01); *A61K 2039/5258* (2013.01); *C12N 2710/16423* (2013.01); *C12N 2710/16434* (2013.01); *C12N 2760/18134* (2013.01)

(58) Field of Classification Search
CPC .................. A61K 39/245; A61K 39/17; A61K 2039/5258; A61K 39/12; A61P 31/22; C07K 14/005; C12N 2710/16423; C12N 2710/16434; C12N 2760/18134; C12N 2760/18122
See application file for complete search history.

(56) References Cited

U.S. PATENT DOCUMENTS

| | | | |
|---|---|---|---|
| 9,402,895 B2 | 8/2016 | Chang et al. | |
| 2015/0216965 A1* | 8/2015 | Diamond | A61P 31/12 435/320.1 |

FOREIGN PATENT DOCUMENTS

| | | | |
|---|---|---|---|
| WO | 2007/014162 A2 | 2/2007 | |
| WO | WO-2017148928 A1 * | 9/2017 | A61K 39/245 |

OTHER PUBLICATIONS

Nealon K, Newcomb WW, Pray TR, Craik CS, Brown JC, Kedes DH. Lytic replication of Kaposi's sarcoma-associated herpesvirus results in the formation of multiple capsid species: isolation and molecular characterization of A, B, and C capsids from a gammaherpesvirus. J Virol. Mar. 2001;75(6):2866-78. (Year: 2001).*
Whitby D, Marshall VA, Bagni RK, Miley WJ, McCloud TG, Hines-Boykin R, Goedert JJ, Conde BA, Nagashima K, Mikovits J, Dittmer DP, Newman DJ. Reactivation of Kaposi's sarcoma-associated herpesvirus by natural products from Kaposi's sarcoma endemic regions. Int J Cancer. Jan. 15, 2007;120(2):321-8. (Year: 2007).*
Szymczak-Workman AL, Vignali KM, Vignali DA. Design and construction of 2A peptide-linked multicistronic vectors. Cold Spring Harb Protoc. Feb. 1, 2012;2012(2):199-204. (Year: 2012).*
Akula, S. M., et al., "Human herpesvirus 8 envelope-associated glycoprotein B interacts with heparan sulfate-like moieties," Virol. 284:235-249 (2001).
Akula, S. M., et al., "Integrin α3β1 (CD 49c/29) is a cellular receptor for Kaposi's sarcoma-associated herpesvirus (KSHV/HHV-8) entry into the target cells," Cell 108:407-419 (2002).
Barasa, A. K., et al., "BALB/c mice immunized with a combination of virus-like particles incorporating Kaposi sarcoma-associated herpesvirus (KSHV) envelope glycoproteins gpK8.1, GB, and gH/gL induced comparable serum neutralizing antibody activity to UV-inactivated KSHV," Oncotarget 8(21):34481-34497 (2017).
Barozzi, P., et al., "Changes in the immune responses against human herpesvirus-8 in the disease course of posttransplant Kaposi sarcoma," Transplantation 86:738-744 (2008).
Bechtel, J. T., et al., "Host and viral proteins in the virion of Kaposi's sarcoma-associated herpesvirus," J. Virol. 79(8):4952-4964 (2005).

(Continued)

*Primary Examiner* — Rachel B Gill
(74) *Attorney, Agent, or Firm* — Perkins Coie LLP; Lara J. Dueppen; Gregory J. Logan

(57) ABSTRACT

Vaccine compositions comprising a single KSHV-LP comprising two or more KSHV glycoproteins and/or one or more T cell antigens and methods of preventing or treating KSHV infections using the vaccine compositions. An expression system or a single expression vector for co-expressing two or more KSHV glycoproteins simultaneously to generate a vaccine comprising a single virus-like particle. The expression system may include a single plasmid inserted with two or more nucleic acid sequences that encode two or more KSHV glycoproteins linked by one or more linking sequences such that the KSHV glycoproteins are co-expressed simultaneously.

16 Claims, 9 Drawing Sheets
Specification includes a Sequence Listing.

(56) References Cited

OTHER PUBLICATIONS

Bray, F., et al., "Global cancer statistics 2018: GLOBOCAN estimates of incidence and mortality worldwide for 36 cancers in 185 countries," CA Cancer J. Clin. 68:394-424 (2018).
Broering, T. J., et al., "Identification and characterization of broadly neutralizing human monoclonal antibodies directed against the E2 envelope glycoprotein of hepatitis C virus," J. Virol. 83(23):12473-12482 (2009).
Brulois, K. F., et al., "Construction and manipulation of a new Kaposi's sarcoma-associated herpesvirus bacterial artificial chromosome clone," J. Virol. 86(18):9708-9720 (2012).
Carroll, M. W., et al., "Host range and cytopathogenicity of the highly attenuated MVA strain of vaccinia virus: Propagation and generation of recombinant viruses in a nonhuman mammalian cell line," Virol. 238:198-211 (1997).
Cesarman, E., et al., "Kaposi's sarcoma-associated herpesvirus-like DNA sequences in AIDS-related body-cavity-based lymphomas," N. Engl. J. Med. 332:1186-1191 (1995).
Chakraborty, S., et al., "Kaposi's sarcoma-associated herpesvirus interacts with EphrinA2 receptor to amplify signaling essential for productive infection," PNAS E1163-E1172 (2012).
Chandran, B., "Minireview: Early events in Kaposi's sarcoma-associated herpesvirus infection of target cells," J. Virol. 84(5):2188-2199 (2010).
Chang, H., et al., "Non-human primate model of Kaposi's sarcoma-associated herpesvirus infection," PLoS Pathog. 5(10):e1000606 (2009).
Chang, Y., et al., "Identification of herpesvirus-like DNA sequences in AIDS-associated Kaposi's sarcoma," Science 266:1865-1869 (1994).
Chiuppesi, F., et al., "Multiantigenic modified vaccinia virus ankara vaccine vectors to elicit potent humoral and cellular immune responses against human cytomegalovirus in mice," J. Virol. 92:e01012-01018 (2018).
Dittmer, D. P., et al., "Kaposi sarcoma-associated herpesvirus: immunobiology, oncogenesis, and therapy," J. Clin. Invest. 126(9):3165-3175 (2016).
Fouts, A. E., et al., "Antibodies against the gH/gL/UL128/UL130/UL131 complex comprise the majority of the anti-cytomegalovirus (Anti-CMV) neutralizing antibody response in CMV hyperimmune globulin," J. Virol. 86(13):7444-7447 (2012).
Gantt, S., et al., "Prospective characterization of the risk factors for transmission and symptoms of primary human herpesvirus infections among Ugandan infants," J. Infect. Dis. 214:36-44 (2016).
Genini, E., et al., "Serum antibody response to the gH/gL/pUL128-131 five-protein complex of human cytomegalovirus (HCMV) in primary and reactivated HCMV infections," J. Clin. Virol. 52:113-118 (2011).
Gibson, D. G., et al., "Enzymatic assembly of DNA molecules up to several hundred kilobases," Nat. Meth. 6(5):343-345 (2009).
Goepfert, P. A., et al., "Phase 1 safety and immunogenicity testing of DNA and recombinant modified vaccinia ankara vaccines expressing HIV-1 virus-like particles," J. Infect. Dis. 203:610-619 (2011).
Goepfert, P. A., et al., "Specificity and 6-month durability of immune responses induced by DNA and recombinant modified vaccinia ankara vaccines expressing HIV-1 virus-like particles," J. Infect. Dis. 210:99-110 (2014).
Hahn, A., et al., "The ephrin receptor tyrosine kinase A2 is a cellular receptor for Kaposi's sarcoma-associated herpesvirus," Nat. Med. 18(6):961-966 (2012).
Jacobson, L. P., et al., "Interaction of human immunodeficiency virus type 1 and human herpesvirus type 8 infections on the incidence of Kaposi's sarcoma," J. Infect. Dis. 181:1940-1949 (2000).
Jangalwe, S., et al., "Improved B cell development in humanized NOD-scid IL2Rγ$^{null}$ mice transgenically expressing human stem cell factor, granulocyte-macrophage colony-stimulating factor and interleukin-3," Immun. Inflam. Dis. 4(4):427-440 (2016).
Khodai, T., et al., "Single and combination herpes simplex virus type 2 glycoprotein vaccines adjuvanted with CpG oligodeoxynucleotides or monophosphoryl lipid A exhibit differential immunity that is not correlated to protection in animal models," Clin. Vaccine Immunol. 18(10):1702-1709 (2011).
Kim, J. H., et al., "High cleavage efficiency of a 2A peptide derived from porcine teschovirus-1 in human cell lines, zebrafish and mice," PLoS One 6(4):e18556 (2011).
Koelle, D. M., et al., "Frequent detection of Kaposi's sarcoma-associated herpesvirus (human herpesvirus 8) DNA in saliva of human immunodeficiency virus-infected men: Clinical and immunologic correlates," J. Infect. Dis. 176:94-102 (1997).
Koyano, S., et al., "Glycoprotein M and N of human herpesvirus 8 form a complex and inhibit cell fusion," J. Gen. Virol. 84:1485-1491 (2003).
Kumar, P., et al., "Higher levels of neutralizing antibodies against KSHV in KS patients compared to asymptomatic individuals from Zambia," PLoS One 8(8):e71254 (2013).
Labo, N., et al., "Heterogeneity and breadth of host antibody response to KSHV infection demonstrated by systematic analysis of the KSHV proteome," PLoS Pathog. 10(3):e1004046 (2014).
Lane, J. M., "Mass vaccination and surveillance/containment in the eradication of smallpox," CTMI 304:17-29 (2006).
Mayr, A., et al., "Abstammung, eigenschaften und verwendung des attenuierten vaccinia-stammes MVA," Infection 3:6-14 (1975).
Mesri, E. A., "Kaposi's sarcoma herpesvirus/Human herpesvirus-8 (KSHV/HHV8), and the oncogenesis of Kaposi's sarcoma," Nat. Rev. Cancer 10(10):707-719 (2010).
Minhas, V., et al., "Early childhood infection by human herpesvirus 8 in Zambia and the role of human immunodeficiency virus type 1 coinfection in a highly endemic area," Am. J. Epidemiol. 168(3):311-320 (2008).
Minhas, V., et al., "Primary gamma-herpesviral infection in Zambian children," BMC Infect. Dis. 10:115 (2010).
Morrison, T. G., et al., "Structure and function of a paramyxovirus fusion protein," Biochim. Biophys. Acta 1614:73-84 (2003).
Mulama, D. H., et al., "A multivalent Kaposi sarcoma-associated herpesvirus-like particle vaccine capable of eliciting high titers of neutralizing antibodies in immunized rabbits," Vaccine 37(30):4184-4194 (2019).
Myoung, J., et al., "Generation of a doxycycline-inducible KSHV producer cell line of endothelial origin: Maintenance of tight latency with efficient reactivation upon induction," J. Virol. Methods 174(1-2):12-21 (2011).
Nicol, S. M., et al., "Primary B lymphocytes infected with Kaposi's sarcoma-associated herpesvirus can be expanded in vitro and are recognized by LANA-specific CD4+ T cells," J. Virol. 90(8):3849-3859 (2016).
Ogembo, J. G., et al., "A chimeric EBV gp350/220-based VLP replicates the virion B-cell attachment mechanism and elicits long-lasting neutralizing antibodies in mice," J. Transl. Med. 13:50 (2015).
Pantua, H. D., et al., "Requirements for the assembly and release of Newcastle disease virus-like particles," J. Virol. 80(22):11062-11073 (2006).
Perez, E. M., et al., "Novel Epstein-Barr virus-like particles incorporating gH/gL-EBNA1 or GB-LMP2 induce high neutralizing antibody titers and EBV-specific T-cell responses in immunized mice," Oncotarget 8(12):19255-19273 (2017).
Purushothaman, P., et al., "KSHV genome replication and maintenance," Front. Microbiol. 7:54 (2016).
Roshan, R., et al., "T-cell responses to KSHV infection: a systematic approach," Oncotarget 8(65):109402-109416 (2017).
Russo, J. J., et al., "Nucleotide sequence of the Kaposi sarcoma-associated herpesvirus (HHV8)," Proc. Natl. Acad. Sci. USA 93:14862-14867 (1996).
Sabbah, S., et al., "T-cell immunity to Kaposi sarcoma-associated herpesvirus: recognition of primary effusion lymphoma by LANA-specific CD4+ T cells," Blood 119(9):2083-2092 (2012).
Soulier, J., et al., "Kaposi's sarcoma-associated herpesvirus-like DNA sequences in multicentric castleman's disease," Blood 86(4):1276-1280 (1995).
Spiller, O. B., et al., "Complement regulation by Kaposi's sarcoma-associated herpesvirus ORF4 protein," J. Virol. 77(1):592-599 (2003).

(56) References Cited

OTHER PUBLICATIONS

Spiller, O. B., et al., "Dissecting the regions of virion-associated Kaposi's sarcoma-associated herpesvirus complement control protein required for complement regulation and cell binding," J. Virol. 80(8):4068-4078 (2006).

Tischer, B. K., et al., "*En passant* mutagenesis: A two step markerless red recombination system," Meth. Mol. Biol. 634:421-430 (2010).

Totonchy, J., et al., "KSHV induces immunoglobulin rearrangements in mature B lymphocytes," PLoS Pathog. 14(4):e1006967 (2018).

Uldrick, T. S., et al., "An interleukin-6-related systemic inflammatory syndrome in patients coinfected with Kaposi sarcoma-associated herpesvirus and HIV but without multicentric Castleman disease," Clin. Infect. Dis. 51(3):350-358 (2010).

United States Patent and Trademark Office, International Search Report and Written Opinion dated Jul. 20, 2020 for PCT/US20/19207, 10 pages.

Veettil, M. V., et al., "Interaction of KSHV with host cell surface receptors and cell entry," Viruses 6:4024-4046 (2014).

Wabinga, H. R., et al., "Cancer in Kampala, Uganda, in 1989-1991: Changes in incidence in the era of AIDS," Int. J. Cancer 54:26-36 (1993).

Wang, L.X., et al., "Humanized-BLT mouse model of Kaposi's sarcoma-associated herpesvirus infection," PNAS 111(8):3146-3151 (2014).

Wang, X.J., et al., "Structure and function study of paramyxovirus fusion protein heptad repeat peptides," Arch. Biochem. Biophys. 436:316-322 (2005).

Webster-Cyriaque, J., et al., "Epstein-barr virus and human herpesvirus 8 prevalence in human immunodeficiency virus-associated oral mucosal lesions," J. Infect. Dis. 175:1324-1332 (1997).

Wu, T.T., et al., "Vaccine prospect of Kaposi sarcoma-associated herpesvirus," Curr. Opin. Virol. 2:482-488 (2012).

Wussow, F., et al., "Human cytomegalovirus vaccine based on the envelope gH/gL pentamer complex," PLoS Pathog. 10(11):e1004524 (2014).

Zhu, F. X., et al., "Virion proteins of Kaposi's sarcoma-associated herpesvirus," J. Virol. 79(2):800-811 (2005).

Zhu, L., et al., "Characterization of human herpesvirus-8 K8.1A/B glycoproteins by monoclonal antibodies," Virol. 262:237-249 (1999).

\* cited by examiner

Fig. 2A

Untransfected | Isotype Control | gpK8.1-gB-gL-gH +HR2 | gpK8.1-gB-gL-gH -HR2 mAb anti-K8.1-Alexa Fluor 488

Fig. 2B

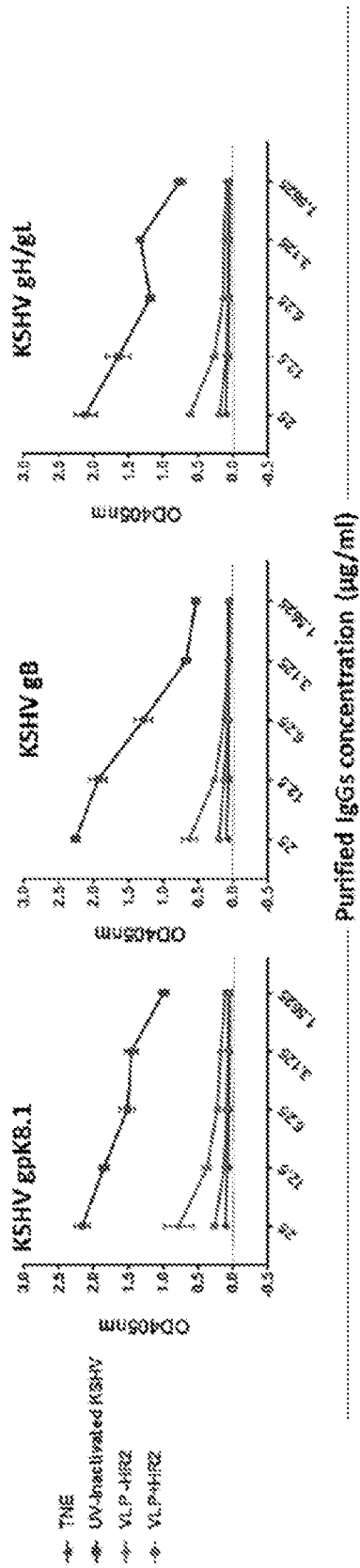

SEQUENCE LISTING

<160> NUMBER OF SEQ ID NOS: 28

<210> SEQ ID NO 1
<211> LENGTH: 489
<212> TYPE: PRT
<213> ORGANISM: Artificial Sequence
<220> FEATURE:
<223> OTHER INFORMATION: full-length NP sequence

<400> SEQUENCE: 1

Met Ser Ser Val Phe Asp Glu Tyr Glu Gln Leu Leu Ala Ala Gln Thr
1               5                   10                  15

```
Arg Pro Asn Gly Ala His Gly Gly Glu Lys Gly Ser Thr Leu Lys
                20                  25                  30

Val Glu Val Pro Val Phe Thr Leu Asn Ser Asp Asp Pro Glu Asp Arg
            35                  40                  45

Trp Asn Phe Val Val Phe Cys Leu Arg Ile Ala Val Ser Glu Asp Ala
 50                  55                  60

Asn Lys Pro Leu Arg Gln Gly Ala Leu Ile Ser Leu Leu Cys Ser His
 65                  70                  75                  80

Ser Gln Val Met Arg Asn His Val Ala Leu Ala Gly Lys Gln Asn Glu
                85                  90                  95

Ala Thr Leu Ala Val Leu Glu Ile Asp Gly Phe Thr Asn Ser Val Pro
                100                 105                 110

Gln Phe Asn Asn Thr Ser Gly Val Ser Glu Glu Arg Ala Gln Arg Phe
            115                 120                 125

Met Met Ile Ala Gly Ser Leu Pro Arg Ala Cys Ser Asn Gly Thr Pro
    130                 135                 140

Phe Ile Thr Ala Gly Val Glu Asp Asp Ala Pro Glu Asp Ile Ile Asp
145                 150                 155                 160

Thr Leu Glu Arg Ile Leu Ser Ile Gln Ala Gln Val Trp Val Thr Val
                165                 170                 175

Ala Lys Ala Met Thr Ala Tyr Glu Thr Ala Asp Glu Ser Glu Thr Arg
                180                 185                 190

Arg Ile Asn Lys Tyr Met Gln Gln Gly Arg Val Gln Lys Lys Tyr Ile
            195                 200                 205

Leu His Pro Val Cys Arg Ser Ala Ile Gln Leu Thr Ile Arg Gln Ser
    210                 215                 220

Leu Ala Val Arg Ile Phe Leu Val Ser Glu Leu Lys Arg Gly Arg Asn
225                 230                 235                 240

His Ala Gly Gly Ser Ser Thr Tyr Tyr Asn Leu Val Gly Asp Val Asp
                245                 250                 255

Ser Tyr Ile Arg Asn Thr Gly Leu Thr Ala Phe Phe Leu Thr Leu Lys
                260                 265                 270

Tyr Gly Ile Asn Thr Lys Thr Ser Ala Leu Ala Leu Ser Ser Leu Ala
            275                 280                 285

Gly Asp Ile Gln Lys Met Lys Gln Leu Met Arg Leu Tyr Arg Met Lys
    290                 295                 300

Gly Asp Asn Ala Pro Tyr Met Thr Leu Leu Gly Asp Ser Asp Gln Met
305                 310                 315                 320

Ser Phe Ala Pro Ala Glu Tyr Ala Gln Leu Tyr Ser Phe Ala Met Ala
                325                 330                 335

Met Ala Ser Val Leu Asp Lys Gly Thr Gly Lys Tyr Gln Phe Ala Arg
                340                 345                 350

Asp Phe Met Ser Thr Ser Phe Trp Arg Leu Gly Val Glu Tyr Ala Gln
            355                 360                 365

Ala Gln Gly Ser Ser Ile Asn Glu Asp Met Ala Ala Glu Leu Lys Leu
    370                 375                 380

Thr Pro Ala Ala Arg Arg Gly Leu Ala Ala Ala Gln Arg Val Ser
385                 390                 395                 400

Glu Glu Thr Ser Ser Met Asp Ile Pro Thr Gln Ala Gly Val Leu
                405                 410                 415

Thr Gly Leu Ser Asp Gly Gly Pro Gln Ala Pro Gln Gly Gly Ser Asn
                420                 425                 430
```

```
Arg Ser Gln Gly Arg Pro Asp Ala Gly Asp Gly Glu Thr Gln Phe Leu
            435                 440                 445

Asp Leu Met Arg Ala Val Ala Asn Ser Met Arg Glu Ala Pro Asn Ser
        450                 455                 460

Val Gln Ser Thr Thr Gln Pro Glu Pro Pro Thr Pro Gly Pro Ser
465             470                 475                 480

Gln Asp Asn Asp Thr Asp Trp Gly Tyr
                485

<210> SEQ ID NO 2
<211> LENGTH: 26
<212> TYPE: PRT
<213> ORGANISM: Artificial Sequence
<220> FEATURE:
<223> OTHER INFORMATION: 26 AA fragment of NP sequence

<400> SEQUENCE: 2

Ser Val Gln Ser Thr Thr Gln Pro Glu Pro Pro Thr Pro Gly Pro
1               5                   10                  15

Ser Gln Asp Asn Asp Thr Asp Trp Gly Tyr
            20                  25

<210> SEQ ID NO 3
<211> LENGTH: 7
<212> TYPE: PRT
<213> ORGANISM: Artificial Sequence
<220> FEATURE:
<223> OTHER INFORMATION: fusion protein

<400> SEQUENCE: 3

Gly Ala Ala Gly Ala Gly Ala
1               5

<210> SEQ ID NO 4
<211> LENGTH: 4
<212> TYPE: PRT
<213> ORGANISM: Artificial Sequence
<220> FEATURE:
<223> OTHER INFORMATION: signal peptide

<400> SEQUENCE: 4

Lys Lys Lys Arg
1

<210> SEQ ID NO 5
<211> LENGTH: 4
<212> TYPE: PRT
<213> ORGANISM: Artificial Sequence
<220> FEATURE:
<223> OTHER INFORMATION: signal peptide

<400> SEQUENCE: 5

Arg Lys Lys Arg
1

<210> SEQ ID NO 6
<211> LENGTH: 57
<212> TYPE: DNA
<213> ORGANISM: Artificial Sequence
<220> FEATURE:
<223> OTHER INFORMATION: gpK8.1-gB linker

<400> SEQUENCE: 6
gctactaact tcagcctgct gaagcaggct ggagacgtgg aggagaaccc tggacct      57
```

<210> SEQ ID NO 7
<211> LENGTH: 19
<212> TYPE: PRT
<213> ORGANISM: Artificial Sequence
<220> FEATURE:
<223> OTHER INFORMATION: gpK8.1-gB linker

<400> SEQUENCE: 7

Ala Thr Asn Phe Ser Leu Leu Lys Gln Ala Gly Asp Val Glu Glu Asn
1               5                   10                  15

Pro Gly Pro

<210> SEQ ID NO 8
<211> LENGTH: 57
<212> TYPE: DNA
<213> ORGANISM: Artificial Sequence
<220> FEATURE:
<223> OTHER INFORMATION: gB-gL linker

<400> SEQUENCE: 8
gcgactaact tctcattgtt gaaacaggca ggagatgtcg aagagaaccc tggtcca      57

<210> SEQ ID NO 9
<211> LENGTH: 19
<212> TYPE: PRT
<213> ORGANISM: Artificial Sequence
<220> FEATURE:
<223> OTHER INFORMATION: gB-gL linker

<400> SEQUENCE: 9

Ala Thr Asn Phe Ser Leu Leu Lys Gln Ala Gly Asp Val Glu Glu Asn
1               5                   10                  15

Pro Gly Pro

<210> SEQ ID NO 10
<211> LENGTH: 57
<212> TYPE: DNA
<213> ORGANISM: Artificial Sequence
<220> FEATURE:
<223> OTHER INFORMATION: gL-gH linker

<400> SEQUENCE: 10
gcaacgaatt tctcccttct aaagcaagcc ggtgacgtgg aggagaatcc cggaccc      57

<210> SEQ ID NO 11
<211> LENGTH: 19
<212> TYPE: PRT
<213> ORGANISM: Artificial Sequence
<220> FEATURE:
<223> OTHER INFORMATION: gL-gH linker

<400> SEQUENCE: 11

Ala Thr Asn Phe Ser Leu Leu Lys Gln Ala Gly Asp Val Glu Glu Asn
1               5                   10                  15

Pro Gly Pro

<210> SEQ ID NO 12
<211> LENGTH: 39
<212> TYPE: DNA
<213> ORGANISM: Artificial Sequence
<220> FEATURE:
<223> OTHER INFORMATION: KSHV K8.1-Fc-His forward cloning primer

<400> SEQUENCE: 12
aaaaagcggc cgcgccacca tgagttccac acagattcg                                  39

<210> SEQ ID NO 13
<211> LENGTH: 35
<212> TYPE: DNA
<213> ORGANISM: Artificial Sequence
<220> FEATURE:
<223> OTHER INFORMATION: KSHV K8.1-Fc-His reverse cloning primer

<400> SEQUENCE: 13
aaaaaactag tgtaaagatg ggtccgtatt tctgc                                      35

<210> SEQ ID NO 14
<211> LENGTH: 41
<212> TYPE: DNA
<213> ORGANISM: Artificial Sequence
<220> FEATURE:
<223> OTHER INFORMATION: KSHV gB-Fc-His forward cloning primer

<400> SEQUENCE: 14
aaaaagcggc cgcgccacca tgactcccag gtctagattg g                               41

<210> SEQ ID NO 15
<211> LENGTH: 38
<212> TYPE: DNA
<213> ORGANISM: Artificial Sequence
<220> FEATURE:
<223> OTHER INFORMATION: KSHV gB-Fc-His reverse cloning primer

<400> SEQUENCE: 15
aaaaaactag ttttaataaa atttatgaat ccggtaac                                   38

<210> SEQ ID NO 16
<211> LENGTH: 49
<212> TYPE: DNA
<213> ORGANISM: Artificial Sequence
<220> FEATURE:
<223> OTHER INFORMATION: KSHV gH-gL Gibson forward cloning primer

<400> SEQUENCE: 16
ttctcgagga tccgcggccg cgccaccatg gggatctttg cgctatttg                       49

<210> SEQ ID NO 17
<211> LENGTH: 45
<212> TYPE: DNA
<213> ORGANISM: Artificial Sequence
<220> FEATURE:
<223> OTHER INFORMATION: KSHV gH-gL Gibson reverse cloning primer

<400> SEQUENCE: 17
gcatgtgtga gttttgtcac tagttgcgcg tcttctatac atgcc                           45

<210> SEQ ID NO 18
<211> LENGTH: 21
<212> TYPE: DNA
<213> ORGANISM: Artificial Sequence
<220> FEATURE:
<223> OTHER INFORMATION: FC-His sequencing primer

<400> SEQUENCE: 18
gtcgaggtct cgacggtatc g                                                     21

<210> SEQ ID NO 19
<211> LENGTH: 22
<212> TYPE: DNA
<213> ORGANISM: Artificial Sequence

```
<220> FEATURE:
<223> OTHER INFORMATION: FC-His sequencing primer

<400> SEQUENCE: 19
ctctataggc accccctttt gg                                           22

<210> SEQ ID NO 20
<211> LENGTH: 22
<212> TYPE: DNA
<213> ORGANISM: Artificial Sequence
<220> FEATURE:
<223> OTHER INFORMATION: FC-His sequencing primer

<400> SEQUENCE: 20
cgcgcgccac cagacataat ag                                           22

<210> SEQ ID NO 21
<211> LENGTH: 19
<212> TYPE: DNA
<213> ORGANISM: Artificial Sequence
<220> FEATURE:
<223> OTHER INFORMATION: FC-His sequencing primer

<400> SEQUENCE: 21
gctttaataa gatctctag                                               19

<210> SEQ ID NO 22
<211> LENGTH: 20
<212> TYPE: DNA
<213> ORGANISM: Artificial Sequence
<220> FEATURE:
<223> OTHER INFORMATION: FC-His sequencing primer

<400> SEQUENCE: 22
tgctgggcac ggtgggcatg                                              20

<210> SEQ ID NO 23
<211> LENGTH: 22
<212> TYPE: DNA
<213> ORGANISM: Artificial Sequence
<220> FEATURE:
<223> OTHER INFORMATION: FC-His sequencing primer

<400> SEQUENCE: 23
gggtcttttc tgcagaagct tg                                           22

<210> SEQ ID NO 24
<211> LENGTH: 21
<212> TYPE: DNA
<213> ORGANISM: Artificial Sequence
<220> FEATURE:
<223> OTHER INFORMATION: FC-His sequencing primer

<400> SEQUENCE: 24
ctgaccaaga accaggtcag c                                            21

<210> SEQ ID NO 25
<211> LENGTH: 21
<212> TYPE: DNA
<213> ORGANISM: Artificial Sequence
<220> FEATURE:
<223> OTHER INFORMATION: FC-His sequencing primer

<400> SEQUENCE: 25
gacgctcaag tcagaggtgg c                                            21
```

```
<210> SEQ ID NO 26
<211> LENGTH: 23
<212> TYPE: DNA
<213> ORGANISM: Artificial Sequence
<220> FEATURE:
<223> OTHER INFORMATION: FC-His sequencing primer

<400> SEQUENCE: 26
ctccccgtcg tgtagataac tac                                             23

<210> SEQ ID NO 27
<211> LENGTH: 22
<212> TYPE: DNA
<213> ORGANISM: Artificial Sequence
<220> FEATURE:
<223> OTHER INFORMATION: FC-His sequencing primer

<400> SEQUENCE: 27
caatattatt gaagcattta tc                                              22

<210> SEQ ID NO 28
<211> LENGTH: 21
<212> TYPE: DNA
<213> ORGANISM: Artificial Sequence
<220> FEATURE:
<223> OTHER INFORMATION: FC-His sequencing primer

<400> SEQUENCE: 28
tgcgtaagga gaaaataccg c                                               21
```

MULTIVALENT KAPOSI SARCOMA-ASSOCIATED HERPESVIRUS-LIKE PARTICLES AND USES THEREOF

PRIORITY CLAIM

The present invention is a U.S. National Phase Application of International Patent Application No. PCT/US2020/019207, filed Feb. 21, 2020, which claims the benefit of U.S. Provisional Patent Application No. 62/809,481, filed Feb. 22, 2019, the content of which are incorporated herein by reference in their entirety.

GOVERNMENT INTEREST

This invention was made with government support under Grant No. K01CA184388, awarded by the National Institutes of Health (NIH). The government has certain rights in the invention.

SEQUENCE LISTING

This application contains a Sequence Listing, which was submitted in ASCII format via EFS-Web, and is hereby incorporated by reference in its entirety. The ASCII copy, created on Aug. 13, 2021, is named SequenceListing.txt and is 10 kilobytes in size.

BACKGROUND

Infection with Kaposi sarcoma-associated herpesvirus (KSHV), also known as human herpesvirus-8 (HHV-8) is estimated to account for over 44,000 new cancer cases and 20,000 deaths globally every year (1). KSHV is associated with the endothelial-based Kaposi sarcoma (KS) and two rare B cell-based lymphomas: primary effusion lymphoma and multicentric Castleman disease, as well as KSHV inflammatory cytokine syndrome (2-5), particularly in immunosuppressed patients. KS is the most common cancer among persons with AIDS and is often incurable with current treatment options. Unlike other human herpesviruses (HHVs), KSHV is not ubiquitous but is highly prevalent in some areas, such as sub-Saharan Africa where KS is the leading cancer among people living with HIV/AIDS (1, 2, 6). Despite the HIV/AIDS pandemic and KSHV endemicity in Africa, the Mediterranean region and some parts of South America, efforts to develop a prophylactic and/or therapeutic vaccine against KSHV and its associated malignancies have been limited, with no clinical vaccine trial ever reported (7). Hence, there is a need for a vaccine to prevent and treat KSHV infections.

BRIEF DESCRIPTION OF THE DRAWINGS

FIG. 1A shows schematic representation of pCAGGS-gpK8.1-F-2A-gB-F-2A-WTgL-2A-gH-F-/+HR2 plasmids (not drawn to scale). A single transcript was synthesized to express the gpK8.1 ectodomain (ED) fused to NDV fusion protein (F) transmembrane/cytoplasmic (TM/CT) domains (gpK8.1-F), the gB ED fused to NDV F TM/CT (gB-F), and the gH ED fused to NDV F TM/CT (gH-F), each with or without heptad region 2 (+/−HR2), and with full-length wild-type gL (WTgL) inserted between the gB and gH sequences. Sequence fidelity was confirmed using Sanger sequencing. The numbers shown represent corresponding amino acid numbers of the EDs. FIG. 1B shows expression of gpK8.1-gB-WTgL-gH-/+HR2 in HEK-293 and CHO cells. 106 cells from HEK-293 or CHO cells were seeded in a six-well plate and transfected with 2 µg of pCAGGS-gpK8.1-F-2A-gB-F-2A-WTgL-2A-gH-F-/+HR2 or pCAGGS-gpK8.1-F+HR2 (positive control). Transfection efficiency was evaluated 48 hours post-transfection by staining transfected HEK-293 and CHO cells with gpK8.1 mAb, followed by secondary antibody goat-anti-mouse IgG conjugated to AF488. Unstained cells, cells stained with secondary antibody alone (isotype control), and untransfected cells served as negative controls, and gpK8.1-transfected cells served as positive control. Cells were analyzed using FACS by acquiring 10,000 events.

FIGS. 2A-2D show generation of stable CHO cells expressing gpK8.1-gB-WTgL-gH+/−HR2 proteins and production and characterization of purified KSHV-LPs. FIG. 2A shows generation of stable CHO gpK8.1-gB-WTgL-gH+/−HR2 cells. CHO cells were transfected with 2 µg of pCAGGS-gpK8.1-2A-gB-2A-WTgL-2A-gH-F+/−HR2. Forty-eight hours post-transfection, cells were maintained in selection media supplemented with puromycin (5 µg/ml) until colonies of puromycin-resistant cells were formed. Stable cells were harvested, re-suspended in 1×PBS and stained as in FIG. 1B. Stained cells were live-sorted using FACS five times to a purity of ~50% of K8.1-expressing cells. FIG. 2B is a schematic showing of the production of KSHV-LPs. KSHV gpK8.1-gB-WTgL-gH+/−HR2 stable CHO cells were co-transfected with pCAGGS NDV NP and pCAGGS NDV M plasmids. Supernatants from transfected cells were collected and clarified and KSHV-LPs were pelleted and sucrose-gradient purified as described in the working examples. FIG. 2C shows the immunoblot analysis of purified KSHV-LPs. Un-transfected CHO cells, KSHV gpK8.1-gB-WTgL-gH+/−HR2 stable CHO cells (CHO KSHV-LPs+/−HR2), and purified KSHV-LPs+/−HR2 were resolved on a 4-12% SDS polyacrylamide gel, transferred to a polyvinylidene fluoride membrane, and analyzed by immunoblot using rabbit polyclonal (anti-2A or anti-NDV) or mouse monoclonal (anti-gpK8.1 or anti-gH/gL) antibodies as indicated. FIG. 2D shows the structural and morphological characterization of KSHV-LPs by TEM. rKSHV-eGFP.219 and KSHV-LPs+/−HR2 were fixed in 4% paraformaldehyde and absorbed to glow-discharged, carbon-coated, 200-mesh EM grids. EM images were collected using an FEI Tecnai 12 TEM and recorded with a Gatan 2×2 k CCD camera at a magnification of 21,000× and a defocus value of ~1.5 µm.

FIG. 3A shows Coomassie stain (left) and immunoblot (right) of KSHV gpK8.1, gB, and gH/gL recombinant Fc-His tagged proteins. Fc-6×His-tagged recombinant KSHV gpK8.1, gB, and gH/gL proteins were expressed by transiently transfecting HEK-293 6E cells. Culture media were harvested six days post-transfection by centrifugation and filtration through a 22-µM filter. The Fc-6×His-tagged KSHV proteins in the media were purified using Protein A spin columns, concentrated in PBS using Amicon Ultra 15 centrifugal filter units, and quantified using a nanodrop spectrophotometer. To confirm the specificity of the proteins, the concentrated proteins were separated on a 4-12% SDS-PAGE and detected by Coomassie blue stain (for molecular weight) or transferred to a polyvinylidene fluoride membrane for immunoblot analysis using monoclonal anti-gpK8.1 or anti-gH/gL or polyclonal goat anti-human Fc (gB) antibodies as indicated. FIG. 3B shows immunization and bleeding schedules of wild-type New Zealand white rabbits. Eight- to 10-week-old rabbits (n=6/treatment) were immunized subcutaneously at Days 0, 28 and 42 with 50 μg of purified KSHV-LPs+/−HR2, UV-inactivated KSHV, or THE buffer, all adsorbed to alum and MPL as adjuvants. Immunized rabbits were bled seven days pre-immunization (−7) and on Days 14, 35, 49, 70, and 90 (terminal bleed). FIG. 3C shows serum KSHV glycoprotein-specific antibody responses. KSHV-glycoprotein IgG-specific antibody titers in sera from immunized rabbits were determined using ELISA with recombinant tagged gpK8.1, gB, and gH/gL proteins; results of quadruplicate replicates for each of the six animals per group are expressed as mean±standard deviation (SD). Differences in antibody titers between all groups were analyzed using a Kruskal-Wallis test; differences between the +HR2 and +HR2 vaccine were assessed using a Mann-Whitney test.

FIGS. 4A-4B show in vitro neutralization capabilities of purified IgGs from rabbits immunized with KSHV-LPs+/−HR2 in diverse cell types. FIG. 4A shows titration of purified IgGs specific to KSHV glycoproteins by ELISA. Purification of IgG antibodies was conducted by pooling equal amounts of Day 49 sera from immunized rabbits (n=6) from each of the four treatment/control groups. KSHV-glycoprotein IgG-specific antibody titer was determined using ELISA with recombinant tagged proteins gpK8.1, gB, and gH/gL as targets; results of quadruplicate replicates are expressed as mean±SD. FIG. 4B shows rKSHV-eGFP.219 titration and neutralization assays in epithelial, fibroblast, endothelial, and B cells. Panel i. rKSHV-eGFP.219 virus titration in diverse cell types. Individual cell lines were seeded overnight at a density of $5 \times 10^5$ in quadruplicate in 48-well-plates. The individual cell lines were then incubated with 5, 10, 20, 30, or 50 μl of the purified virus in a total volume of 100 μl of virus plus serum-free media for 24 hours at 37° C. Infected cells (eGFP+) were quantified using FACS by acquiring a total of 10,000 events. Panel ii. Neutralization activity in HEK-293 cells, HFF-1 cells, HUVEC, and MC116 B cell lines. Neutralization activities were determined by incubating rKSHV-eGFP.219 virus and purified IgGs of varying concentrations (12.5, 25, 50, or 100 μg/ml) from all groups of test animals for 1 hour at 37° C., before being added to previously seeded cells in a 48-well plate. After 1-hour incubation at 37° C., the cells were thoroughly washed three times with 1×PBS before adding growth media. The level of neutralization was determined in the cells after 24 hours using FACS to quantify the number of eGFP+ cells. Cells incubated with virus or with media alone served as positive and negative controls, respectively. Results of quadruplicate replicates are expressed as mean±SD.

FIG. 5 shows schematic diagram of MVA-KSHV-5Ag-VLP construct, it can be obtained by a 2A-linked polycistronic expressing transcript including the gpK8.1 ectodomain (ED) fused to NDV fusion protein (F) transmembrane/cytoplasmic (TM/CT) domains (gpK8.1-F); the gB ED fused to NDV F TM/CT (gB-F); and the gH ED fused to NDV F TM/CT (gH-F) without heptad region 2 (−HR2); and full-length wild-type gL (WTgL) between gB and gH, can be inserted at G1L/18R intergenic region of MVABAC-TK. Additionally, the IGR3 site inserted with NDV NP (28 amino acids) fused with partial LANA1 (937-1124 amino acids) protein of KSHV and to facilitate VLPs formation the Del3 site inserted with NDV M. Promotor mH5 can be utilized for expression of all the transgene in MVABAC-TK.

DETAILED DESCRIPTION

Figure 1A:
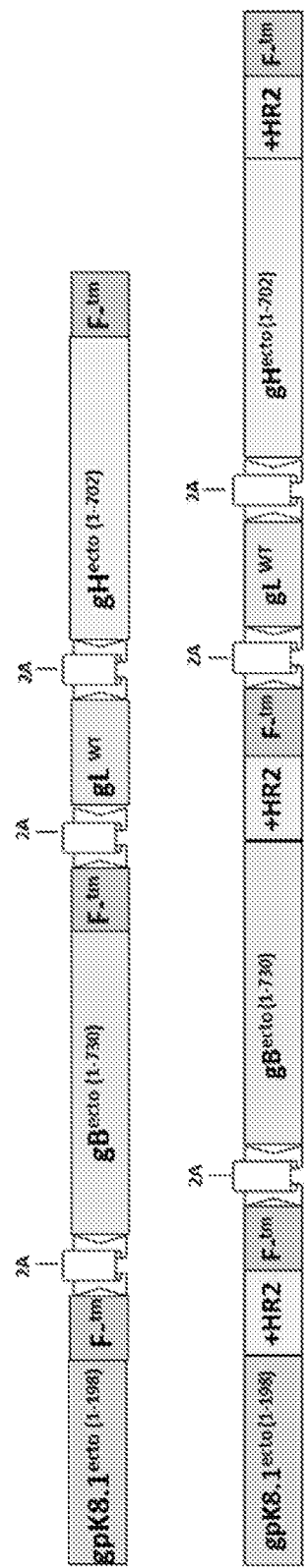
FIGS. 1A-1B show construction and expression of polycistronic plasmids expressing four KSHV glycoproteins.

Expression systems, vectors, vaccines for use in preventing or treating Kaposi sarcoma-associated herpesvirus (KSHV) infections and KSHV-associated conditions or malignancies are provided herein. The polyvalent single KSHV-LP vaccine, which is described in detail below, can stimulate the production of neutralizing antibodies and generate both prophylactic and therapeutic antiviral responses against KSHV infections and KSHV-associated malignancies.

In one aspect, disclosed herein is a novel subunit vaccine that incorporates KSHV envelope glycoproteins required for viral entry in diverse cell types such as gpK8.1, gB, and gH/gL into a single multivalent KSHV-like particle (KSHV-LP). The purified KSHV-LPs were similar in size, shape, and morphology to KSHV virions. In a related aspect, disclosed herein is a method of preventing or treating a subject who is at an elevated risk of KSHV infections and KSHV-associated malignancies or who suffers from KSHV infections and KSHV-associated malignancies. The method comprises administering a therapeutically effective amount of the vaccine disclosed herein to the subject. In yet another related aspect, disclosed herein is a method of neutralizing KSHV infection in vitro in epithelial cells, endothelial cells, fibroblast cells, and B cells, comprising contacting the cells with the KSHV-LPs disclosed herein such that neutralizing antibodies are produced in the cells. In some embodiments, the subject is immunocompromised. In some embodiments, the subject suffers from one or more cancer. In some embodiments, the vaccine further comprises one or more additional glycoproteins such as gM, gN, and ORF4, and/or T cell antigens such as LANA1. The additional glycoproteins and/or T cell antigens can be co-expressed from the same plasmid expressing the KSHV envelope glycoproteins including gpK8.1, gB, and gH/gL or expressed by one or more different plasmids. In some embodiments, the additional glycoproteins and/or T cell antigens can be incorporated into the same, single multivalent KSHV-LP comprising gpK8.1, gB, and gH/gL. In some embodiments, the vaccine is administered to the subject with one or more adjuvants. In some embodiments, one or more booster doses of the vaccine is administered. One of ordinary skill in the art can optimize the doses, intervals, routes of the vaccine administration to achieve the desired immunogenic effects. Several delivery vectors such as modified vaccinia Ankara vectors and adenovirus vectors can be used to deliver KSHV-LPs as live-attenuated vaccines and to elicit high titers of potent neutralizing antibodies that block infection in both in vitro and in vivo infection models better than those found in UV-KSHV immunized rabbits.

Modified vaccinia Ankara (MVA) virus is an attenuated vaccine of a poxvirus (Orthopoxvirus family) generated by about 570 serial passages of the vaccinia Ankara strain on chicken embryo fibroblasts (50). MVA was successfully used in eradication of small pox and elicits durable antibody (Ab) responses (51). Administration of a higher dose of MVA (1×108 TCID50) was safely tolerated in humans (52, 53). MVA and MVA-vectored vaccines displayed a high safety profile, as they are replication-defective in humans, can only replicate in avian cells and are used for propagation (54). MVA has large genome size (~135 kbp) and has lost many of the genes during attenuation, capable of expressing large and multiple transgenes, facilitating expression of KSHV and NDV genes for the formation of KSHV VLPs. Disclosed herein is an MVA-based vaccine design construct to express the KSHV proteins on the surface of non-infectious VLPs. The KSHV VLPs can be formed by the self-assembly and budding of MVA expressed KSHV proteins (K8.1, gB, gL, gH and LANA1) and NDV F, M and NP proteins. KSHV gps are main target for inducing neutralizing antibody response and its display on the VLP surface could efficiently initiate antibody response similar to KSHV infection. The LANA1 protein functions as T-cell antigen for initiating cell mediating immune response against KSHV.

As demonstrated in the working examples, vaccination of rabbits with adjuvanted KSHV-LPs generated strong glycoprotein-specific antibody responses, and purified immunoglobulins from KSHV-LP-immunized rabbits neutralized KSHV infection in epithelial, endothelial, fibroblast, and B cell lines, 60-90% at the highest concentration tested. These findings suggest that KSHV-LPs may be an ideal platform for developing a safe and effective prophylactic KSHV vaccine.

Also demonstrated in the working examples, the co-expression of a single construct of all four glycoproteins interspersed with a 2A self-cleaving peptide for efficient expression and cleavage under a single CMV promoter, and NDV F, NP, and M proteins resulted in the successful self-assembly and release of KSHV-LPs. Purified KSHV-LPs from CHO cells structurally resembled purified KSHV virions in size, shape, and morphology under transmission electron microscope (TEM). In addition, immunoblot assay confirmed that all four KSHV glycoproteins were incorporated into the KSHV-LPs. These data demonstrate that the multivalent VLP expressing four KSHV glycoproteins can be used as a reagent for immunization of animals. The observed effects of pre-existing immunity to KSHV suggest that immunization with the right vaccine candidate may offer protection from KSHV infection and development of KS: patients who become infected with KSHV before contracting HIV (i.e., before immunosuppression) have a significantly reduced incidence of KS compared with those acquiring KSHV after HIV infection (8, 9). Furthermore, KSHV etiology provides a window of opportunity for prevention with a prophylactic vaccine, even in Africa. In Africa, other endemic HHVs achieve widespread transmission and latent infection within the first year of life infecting up to 76% of children. In contrast, few to no children are infected with KSHV by this age or even by five years of age (10-12). In other parts of the world, where KSHV exposure typically occurs during adulthood, transmission is so poor that either repeated contact with the virus, or immunodeficiency, is required to sustain KSHV at >5% population-wide seroprevalence (13, 14). KSHV superinfection in immunocompetent people is also limited, suggesting that some immune protection is conferred among adults (15). Thus, minimal priming of the immune system by a vaccine prior to infection can be achieved to prevent and/or treat KSHV infection and its associated malignancies in developing countries and possibly eradicate KSHV and associated malignancies from developed countries.

Like other HHVs, KSHV encodes five conserved glycoproteins: gB (open reading frame (ORF) 8), gH (ORF 22), gL (ORF 47), gM (ORF 39), and gN (ORF 53) (16, 17). In addition, KSHV also encodes for a unique glycoprotein, gpK8.1, which is the major immunodominant glycoprotein on the virion and is believed to modulate viral tropism for B cells. In the current model of KSHV infection, the virus is thought to first attach to host cell receptors through the non-conserved gpK8.1, which then signals gH/gL to activate the gB fusogen. This infection model is supported by the results of experiments that used neutralizing monoclonal antibodies against gpK8.1 or rKSHV deletion mutants lacking gpK8.1, gB or gH/gL to define the role of each KSHV glycoprotein in infecting various cell types. Because these data provide evidence that different KSHV glycoproteins modulate viral tropism for different cell types, targeting a single glycoprotein in a prophylactic vaccine setting might not completely protect against infection of diverse cell types. The immunization protocol disclosed herein includes gpK8.1, gB, and gH/gL complex into a single vaccine to generate a potent vaccine candidate that elicits neutralizing antibodies blocking KSHV infection of diverse permissive cell types of human origin.

Selection of an appropriate platform is important and unpredictable. Virus-like particles (VLPs) lack the viral genome and typically assemble from viral structural proteins, forming repetitive arrays that resemble a natural virus. As disclosed herein, this platform allows inclusion of multiple selected surface glycoproteins and intracellular T-cell antigens in a polyvalent vaccine.

Due to the oncogenic potential of KSHV DNA (3, 29), it is not feasible to use live attenuated KSHV or any form of inactivated KSHV to elicit immune responses in clinical settings. To circumvent this shortcoming, disclosed herein are virus-like particles (VLPs) that individually incorporate the key KSHV glycoproteins (gpK8.1, gB, or gH/gL complex) into a VLP. These VLPs are immunogenic in immunized wild-type BALB/c mice; however, their immunogenicity in diverse cell types were unknown.

Disclosed herein are the construction, assembly and biochemical characterization of candidate multivalent KSHV-like particle (KSHV-LP) vaccines that incorporate all four key glycoproteins into a single VLP. As demonstrated in the working examples, wild-type New Zealand white rabbits immunized with adjuvanted VLPs unexpectedly elicited strong neutralizing antibodies that prevented in vitro KSHV infection of epithelial cell line, endothelial cell line, fibroblast cell line, and B cell line. Thus, this disclosure relates to a novel vaccine approach with a potential clinical application as a prophylactic vaccine against KSHV infection and its associated malignancies.

Disclosed herein is an immunogenic multi-subunit vaccine comprising a single KSHV-LP that incorporates multiple KSHV glycoproteins including gpK8.1, gB and gH/gL on the virion envelope surface. As demonstrated in the working examples, New Zealand white rabbits were immunized subcutaneously and boosted with the KSHV-LP adjuvanted with both aluminum hydroxide and monophosphoryl lipid A. The anti-KSHV-specific glycoproteins antibody responses were determined by ELISA. Neutralizing antibody titers in sera of immunized rabbits were assessed in various cell types in vitro. The Rabbits immunized with KSHV-LPs elicited high titers of KSHV-specific antibodies that neutralized virus infection in diverse cultured cell lines.

It was previously demonstrated that four glycoproteins, gpK8.1, gB, gH and gL, were highly immunogenic and were able to elicit robust neutralizing antibodies individually and in combination in a mice model (30). However, these antigens were not co-expressed or assembled into a single virus-like particle. As described herein, the expression of the glycoproteins as a single transcript separated by the 2A, self-cleavage peptides, under a single promoter and NDV-M and -NP fused to the KSHV latent protein, LANA1 was sufficient for the production of self-assembling and releasing KSHV-LPs. In addition, the structure of the purified KSHV-LPs resembled that of wild type KSHV in terms of the morphology and size of 100 nm spherical particles with spikes observed under TEM. The inner core of VLP consists of NP fused to LANA1 and surrounded by host cell derived lipid bilayer membrane. Innersurface of membrane is layered with M protein and embedded with transmembrane domain of F protein, that are fused with K8.1, gB or gH glycoprotein of KSHV, displaced on surface of VLP. gL non-covalently bound to N-terminal domain to gH also found on VLP surface.

Although there was no significant difference in the antibodies titers observed between KSHV-LPs+/−HR2 VLPs, KSHV-LPs−HR2 neutralized KSHV infection better, as shown in FIG. 6. The neutralization ability of observed in diverse cell types were comparable to that of UV-KSHV that yielded significant antibody titer. In wild type KSHV, high antibody titers did not translate or correlate to the induction of high titers of neutralizing antibodies. The KSHV-LPs−HR2 vaccine although it generated lower antibody titers, the levels of neutralization of KSHV in vitro was comparable to that of wild type KSHV, while KSHV-LPs+HR2 neutralization levels were lower (FIG. 6). Similar results have been observed in other VLP based vaccine, where the production of high titers of antibodies does not always correlate to high neutralizing response (Boigard et al., 2017). Although not bound with any theory, the difference between KSHV-LPs+ HR2 and −HR2 neutralization activity might be linked to the presence of the HR2 domain, which is involved in protein trimerization. The trimerization of the antigens could have masked the epitopes that are responsible for eliciting neutralizing antibodies.

Thus, disclosed herein is a novel prophylactic and therapeutic polyvalent vaccine comprising two or more KSHV envelope glycoproteins and one or more T cell antigens incorporated into a single virus-like particle. In some embodiments, the vaccine comprises two, three, four, five or more glycoproteins including gpK8.1, gH, gL and gB. In some embodiments, the T cell antigens include LANA1 or an immunogenic fragment thereof. In some embodiments, K8.1, gH/gL or gB or an immunogenic fragment thereof may also show T-cell responses. In some embodiments, in addition to the KSHV glycoproteins and T cell antigens, the vaccine further comprises NDV structural proteins including fusion (F), matrix (M), and nucleocapsid (NP) incorporated into the single VLP. In some embodiments, the vaccine further comprises one or more adjuvants such as alum sulphate and monophosphoryl lipid A.

In some embodiments, disclosed herein is a single vector co-expressing two or more KSHV glycoproteins including gpK8.1, gB, gH, and gL, with each glycoprotein separated from another glycoprotein by 2A sequence. For example, multicistronic 2A sequence is used in a pCAGGS-K8.1-2A-gB-F-2A-gL-WT-2A-gH-F+HR2 vector or a pCAGGS-K8.1-2A-gB-F-2A-gL-WT-2A-gH-F−HR2 vector. The 2A sequence can be, for example, 15 amino acids, 16 amino acids, 17 amino acids, 18 amino acids, 19 amino acids, 20 amino acids, 21 amino acids, 22 amino acids, 23 amino acids, 24 amino acids, or 25 amino acids in length. In some embodiments, a sequence of GAAGAGA is used to generate fusion protein between the antigens. In some embodiments, a full-length NP sequence or a 26-amino acid of NP sequence is used to deliver or package the antigens into the VLPs.

The amino acid sequence of the full-length NP is as follows (SEQ ID NO:1):

```
MSSVFDEYEQLLAAQTRPNGAHGGGEKGSTLKVEVPVFTLNSDDPEDRWNFVVFCLRIAV    60

SEDANKPLRQGALISLLCSHSQVMRNHVALAGKQNEATLAVLEIDGFTNSVPQFNNTSGV   120

SEERAQRFMMIAGSLPRACSNGTPFITAGVEDDAPEDIIDTLERILSIQAQVWVTVAKAM   180

TAYETADESETRRINKYMQQGRVQKKYILHPVCRSAIQLTIRQSLAVRIFLVSELKRGRN   240

HAGGSSTYYNLVGDVDSYIRNTGLTAFFLTLKYGINTKTSALALSSLAGDIQKMKQLMRL   300

YRMKGDNAPYMTLLGDSDQMSFAPAEYAQLYSFAMAMASVLDKGTGKYQFARDFMSTSFW   360

RLGVEYAQAQGSSINEDMAAELKLTPAARRGLAAAAQRVSEETSSMDIPTQQAGVLTGLS   420

DGGPQAPQGGSNRSQGRPDAGDGETQFLDLMRAVANSMREAPNSVQSTTQPEPPPTPGPS   480

QDNDTDWGY                                                      489
```

In some embodiments, the amino acid sequence of the 26 AA fragment of the NP is (SEQ ID NO: 2)
SVQSTTQPEPPPTPGPSQDNDTDWGY.

In some embodiments, disclosed herein is a method of producing KSHV-LPs with a polycistronic vector using one or more 2A sequences in a pCAGGS vector. The 2A sequence can be, for example, 15 amino acids, 16 amino acids, 17 amino acids, 18 amino acids, 19 amino acids, 20 amino acids, 21 amino acids, 22 amino acids, 23 amino acids, 24 amino acids, or 25 amino acids in length. The method can further entail generating fusion protein between the antigens or any other two or more virus latent proteins using a sequence of GAAGAGA (SEQ ID NO:3) to form a NP-fusion protein. In some embodiments, a full-length NP sequence or a 26-amino acid of NP sequence is used to deliver or package KSHV latent proteins into the VLPs.

In some embodiments disclosed herein, the KSHV glycoproteins can be expressed by any suitable expression vectors including plasmid vectors and viral vectors. In some embodiments, modified Ankara vaccinia vector, adeno-associated viruses, baculovirus or messenger RNA can be used for co-expressing two or more KSHV glycoproteins. The individual glycoproteins can be linked by cleavage sequences such that the co-expressed glycoproteins can be self-cleaved and self-assembled into two or more glycoprotein complexes.

In some embodiments, the expression systems or vectors described herein include two or more expression cassettes, each of which includes a single promoter and a sequence that encodes two or more KSHV glycoproteins. As a result, the two or more KSHV glycoproteins are co-expressed simultaneously, i.e., under control of a single promoter, obviating the need for multiple promoters or vectors. In certain embodiments, each expression cassette includes two, three, four, five, or even higher numbers of glycoproteins, the expression of which are under control of a single promoter. In some embodiments, a vector may include more than one such expression cassette.

In some embodiments, 2A signal sequences that encode for the 2A peptide of food-and-mouth disease virus (F2A), equine rhinitis A virus (E2A), porcine teschovirus-1 (P2A), Thoseaasigna virus (T2A), cytoplasmic polyhedrosis virus (BmCPV 2A), or flacherie virus (BmIFV 2A) can be used to link multiple genes under a single promoter. 2A signal sequences have been found in picornaviruses, insect viruses and type C rotaviruses. In some embodiments, a self-cleavage 2A peptide-derived sequence from Picornaviruses is used to co-express the KSHV glycoproteins. Bicistronic or multicistronic expression vectors can be used to express more than one gene product within a cell. Various suitable eukaryotic cell promoters can be used, including but not limited to, immediate-early I promoter of human CMV or the chicken beta actin promoter, promoters of vaccinia virus (mH5, pSyn, P11, p7.5), etc.

Additionally, a furin cleavage site preceding the 2A signal sequences can be incorporated to remove the 2A peptides following self-processing of the 2A-linked polyproteins. Furin is an enzyme that occurs in the Golgi apparatus and cleaves at very short signal peptides such as KKKR (SEQ ID NO:4) or RKKR (SEQ ID NO:5) motif. Furin cleavage contributes to protein processing and maturation. These short signal peptides can be added to the N-terminus of the 18-22 amino acid long 2A skipping signals so that they are removed following 2A-mediated processing of the KSHV envelope glycoproteins, except for one or two remaining amino acids. The resultant product can be even more "native." Although it is preferred that the 2A-linked glycoproteins are expressed all from one vector through the use of one or more expression cassettes, it is also possible to express the 2A-linked subunits from two or more separate vectors.

By exploiting the ribosomal skipping mechanism conferred by 2A peptides, an approach of co-expressing the KSHV glycoproteins as only one or two self-processing polyproteins is disclosed herein. The 2A ribosomal skipping system is widely-used to express multi-protein complexes due to the relative small sizes of 2A peptides (18-22 amino acids) and because it allows stoichiometric expression of the individual 2A-linked subunits. In some embodiments, P2A-linked DNA sequences of two or more KSHV glycoproteins are co-expressed and efficiently cleaved and transported to the cell surface. In some embodiments, the DNA sequences encoding the KSHV glycoproteins are codon-optimized. In some embodiments, the co-expressed KSHV glycoproteins are self-assembled into surface complexes.

According to the embodiments described herein, an immunization regimen is provided. The immunization regimen includes VLPs comprising two or more KSHV glycoproteins and one or more T cell antigens. The immunization regimen may be administered via prime/boost homologous (e.g. using only the same vaccine type) or heterologous (e.g. using different vaccine types) vaccination. The immunization regimen may be administered in a dose vaccination schedule involving two or more immunizations, which may be administered 2 weeks to 6 months apart. Other suitable immunization schedules or regimens that are known in the art may be used according to the embodiments described herein by those skilled in the art.

The vaccine composition as described herein may comprise a therapeutically effective amount of a VLP as described herein, and may further comprise a pharmaceutically acceptable carrier according to a standard method. Examples of acceptable carriers include physiologically acceptable solutions, such as sterile saline and sterile buffered saline.

In some embodiments, the vaccine or pharmaceutical composition may be used in combination with a pharmaceutically effective amount of an adjuvant to enhance the anti-viral effects. Any immunologic adjuvant that may stimulate the immune system and increase the response to a vaccine, without having any specific antigenic effect itself may be used as the adjuvant. Many immunologic adjuvants mimic evolutionarily conserved molecules known as pathogen-associated molecular patterns (PAMPs) and are recognized by a set of immune receptors known as Toll-like Receptors (TLRs). Examples of adjuvants that may be used in accordance with the embodiments described herein include Alum, Freund's complete adjuvant, Freund's incomplete adjuvant, double stranded RNA (a TLR3 ligand), LPS, LPS analogs such as monophosphoryl lipid A (MPL) (a TLR4 ligand), flagellin (a TLR5 ligand), lipoproteins, lipopeptides, single stranded RNA, single stranded DNA, imidazoquinolin analogs (TLR7 and TLR8 ligands), CpG DNA (a TLR9 ligand), Ribi's adjuvant (monophosphoryl-lipid A/trehalose dicorynoycolate), glycolipids (α-GalCer analogs), unmethylated CpG islands, oil emulsion, liposomes, virosomes, saponins (active fractions of saponin such as QS21), muramyl dipeptide, alum, aluminum hydroxide, squalene, BCG, cytokines such as GM-CSF and IL-12, chemokines such as MIP 1-α and RANTES, activating cell surface ligands such as CD40L, N-acetylmuramine-L-alanyl-D-isoglutamine (MDP), and thymosin a1. The amount of adjuvant used can be suitably selected according to the degree of symptoms, such as softening of the skin, pain, erythema, fever, headache, and muscular pain, which might be expressed as part of the immune response in humans or animals after the administration of this type of vaccine.

In further embodiments, use of various other adjuvants, drugs or additives with the vaccine of the invention, as discussed above, may enhance the therapeutic effect achieved by the administration of the vaccine or pharmaceutical composition. The pharmaceutically acceptable carrier may contain a trace amount of additives, such as substances that enhance the isotonicity and chemical stability. Such additives should be non-toxic to a human or other mammalian subjects in the dosage and concentration used, and examples thereof include buffers such as phosphoric acid, citric acid, succinic acid, acetic acid, and other organic acids, and salts thereof; antioxidants such as ascorbic acid; low molecular weight (e.g., less than about 10 residues) polypeptides (e.g., polyarginine and tripeptide) proteins (e.g., serum albumin, gelatin, and immunoglobulin); amino acids (e.g., glycine, glutamic acid, aspartic acid, and arginine); monosaccharides, disaccharides, and other carbohydrates (e.g., cellulose and derivatives thereof, glucose, mannose, and dextrin), chelating agents (e.g., EDTA); sugar alcohols (e.g., mannitol and sorbitol); counterions (e.g., sodium); nonionic surfactants (e.g., polysorbate and poloxamer); antibiotics; and PEG.

The vaccine or pharmaceutical composition containing the KSHV-LPs described herein may be stored as an aqueous solution or a lyophilized product in a unit or multiple dose container such as a sealed ampoule or a vial.

The expression systems, vectors and vaccines described herein may be used to treat or prevent a KSHV infection or conditions associated with KSHV infection such as an endothelial based Kaposi sarcoma, B cell-based lymphomas such as primary effusion lymphoma and multicentric Castleman's disease, carcinomas, and KSHV inflammatory cytokine syndrome.

As used herein, the term "subject" is an animal. In some embodiments, the subject is a mammal. In some embodiments, the subject is human.

The term "an effective amount" as used herein refers to an amount of a composition that produces a desired effect. For example, a population of cells may be infected with an effective amount of a viral vector to study its effect in vitro (e.g., cell culture) or to produce a desired therapeutic effect ex vivo or in vitro. An effective amount of a composition may be used to produce a prophylactic or therapeutic effect in a subject, such as preventing or treating a target condition, alleviating symptoms associated with the condition, or producing a desired physiological effect. In such a case, the effective amount of a composition is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the composition (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the composition is administered alone or in combination with another composition, drug, therapy or other therapeutic method or modality. One skilled in the clinical and pharmacological arts will be able to determine an effective amount or therapeutically effective amount through routine experimentation, namely by monitoring a cell's or subject's response to administration of a composition and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, PA, 2005, which is hereby incorporated by reference as if fully set forth herein.

"Treating" or "treatment" of a condition or an infection may refer to preventing the condition or the infection, slowing the onset or rate of development of the condition or the infection, reducing the risk of developing the condition or the infection, preventing or delaying the development of symptoms associated with the condition or the infection, reducing or ending symptoms associated with the condition or the infection, generating a complete or partial regression of the condition or the infection, or some combination thereof. Treatment may also mean a prophylactic or preventative treatment of a condition or an infection.

In some embodiments, the vaccine or pharmaceutical composition described herein may be used in combination with other known vaccine or pharmaceutical products, such as immune response-promoting peptides, messenger RNAs, viral vectors such as modified vaccinia virus Ankara (MVA), adenovirus, baculovirus, and antibacterial agents (synthetic antibacterial agents). The vaccine or pharmaceutical composition may further comprise other drugs and additives. Examples of drugs or additives that may be used in conjunction with a vaccine or pharmaceutical composition described herein include drugs that aid intracellular uptake of the composition or vaccine disclosed herein, liposome and other drugs and/or additives that facilitate transfection, (e.g., fluorocarbon emulsifiers, cochleates, tubules, golden particles, biodegradable microspheres, and cationic polymers).

In some embodiments, the vaccine composition or pharmaceutical composition described herein may be administered by directly injecting a virus-like particle (VLP) suspension prepared by suspending the VLP in PBS (phosphate buffered saline) or saline into a local site, by nasal or respiratory inhalation, or by intravascular (i.v.) (e.g., intra-arterial, intravenous, and portal venous), subcutaneous (s.c.), intracutaneous (i.c.), intradermal (i.d.), or intraperitoneal (i.p.) administration. The vaccine or pharmaceutical composition disclosed herein may be administered more than once. More specifically, after the initial administration, one or more additional vaccinations may be given as a booster. One or more booster administrations can enhance the desired effect. After the administration of the vaccine or pharmaceutical composition, booster immunization with a pharmaceutical composition containing the VLP as described herein may be performed.

The following examples are provided to better illustrate the claimed invention and are not to be interpreted as limiting the scope of the invention. To the extent that specific materials are mentioned, it is merely for purposes of illustration and is not intended to limit the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

Example 1: Materials and Methods

Animals: Wild-type New Zealand white rabbits and BALB/c wild-type mice were purchased from Pocono Rabbit Farm and Laboratory Inc. and Jackson Laboratory, respectively. Rabbits and mice used for experiments were housed at Pocono Rabbit Farm and Laboratory Inc. and Beckman Research Institute of City of Hope, respectively. Animal procedures were performed in accordance with Pocono Rabbit Farm and Laboratory Inc. and Beckman Research Institute of City of Hope Institutional Animal Care and Use Committee and Institutional Biosafety Committee protocols.

Cells and virus: Chinese hamster ovary (CHO) cells, human embryonic kidney (HEK-293) cells, HEK-293 cells stably expressing Epstein-Barr virus nuclear protein 1 for enhanced ability to produce recombinant proteins (HEK-293 6E), human umbilical vein endothelial cells (HUVEC), human foreskin fibroblast 1 (HFF-1) cells, mouse myeloma cells (P3X63Ag8.653), and B cells derived from the pleural effusion of a patient with undifferentiated lymphoma (MC116) were purchased from the American Type Culture Collection (ATCC, Manassas, VA). Doxycycline-inducible iSLK cells harboring recombinant KSHV.219 expressing enhanced green fluorescent protein from the human elongation factor-1a promoter (iSLD-rKSHV-eGFP.219) (35) were obtained from Dr. D. Dittmer of University of North Carolina, Chapel Hill, NC. CHO, HEK-293, HFF-1, and iSLK-rKHSV.219 cell lines were cultured in Dulbecco's Modified Eagle's Medium (DMEM). P3X63Ag8.653 and MC116 cell lines were cultured in Roswell Park Memorial Institute medium 1640 (RPMI). Hybridomas were cultured in DMEM supplemented with nonessential amino acids (ThermoFisher, Waltham, MA). 1× oxaloacetate-pyruvate-insulin (MilliporeSigma, Burlington, MA), 4 mM glutamine, 1× hypoxanthine-aminopterin-thymidine (MilliporeSigma), 100 IU PS, 1× hybridoma cloning factor (MilliporeSigma), 55 µM 2-mercaptoethanol, and 10% NCTC-109 (ThermoFisher Scientific). Media for culturing iSLK-rKSHV-eGFP.219 cells was supplemented with neomycin (250 µg/mL), hygromycin (400 µg/mL), and puromycin (10 µg/mL) to maintain stable selection of both rKSHV-eGFP.219 and the RTA gene under the pRetro-X Tet-ON inducible system (35). All media were supplemented with 10% heat-inactivated fetal bovine serum (FBS) purchased from MilliporeSigma, 1% L-glutamine and 2% penicillin-streptomycin (ThermoFisher Scientific). HEK-293 6E cells were grown in Freestyle F17 Expression media without FBS (ThermoFisher Scientific). HUVEC cells were grown in endothelial cell growth ready-to-use media (PromoCell, Edmonton, Alberta). Cell lines were routinely tested for mycoplasma using PCR and shown to be negative.

De-identified primary human tonsil specimens were obtained after routine tonsillectomy from the discarded de-identified tissues with approval from the Institutional Review Board of Chapman University. Lymphocytes were extracted by dissection and B cells were isolated and cryopreserved in 90% FBS and 10% DMSO as described (36). Cultured primary B cells were grown in complete RPMI.

To produce virus for infection and neutralization assays, iSLK-rKSHV-eGFP.219 cells were lytically induced and viruses were purified as described (37). In brief, iSLK-rKSHV-eGFP.219 cells were induced by the addition of 2 µg/ml doxycycline (Dox) and 1.5 mM sodium butyrate (NaB) to the culture media for four days and the harvested supernatant was clarified by centrifugation at 2,000×g for 15 minutes at room temperature, followed by filtration through 0.8 µm membrane to remove cellular debris. Virions were pelleted by ultra-centrifugation (25% sucrose solution, SW41 rotor at 10,000×g for 70 minutes at 4° C.). Purified viruses were quantified by titration in each of the cell types used in the infection and neutralization assays.

Antibodies: Primary mouse monoclonal immunoglobulin G2a (IgG2a) anti-gpK8.1 (clone 4A4) (38), which detects the ectodomain of the gpK8.1 protein, was purchased from Santa Cruz Biotechnology (Dallas, TX), and was used for fluorescence-activated cell sorting (FACS), immunoblot, and enzyme-linked immunosorbent assay (ELISA). Primary polyclonal rabbit anti-Newcastle disease virus (NDV) detecting nucleoprotein (NP) was a kind gift of Dr. T. Morrison, University of Massachusetts Medical School, Worcester, MA. Primary polyclonal goat anti-human IgG and rabbit anti-2A protein peptide were purchased from ThermoFisher Scientific and MilliporeSigma, respectively. Primary monoclonal antibodies anti-gpK8.1 (clone 41E7), and anti-gH/gL (clones 54A1 and 57C12) were generated and characterized as outlined below and used in immunoblot and ELISA. HRP-conjugated secondary antibodies goat anti-mouse IgG and goat anti-rabbit IgG, used for immunoblot and ELISA were purchased from MilliporeSigma. Goat Fab-2 anti-mouse IgG (H+L) cross-adsorbed secondary antibody, conjugated to Alexa Fluor 488 (AF488), was purchased from ThermoFisher Scientific and used for FACS.

Construction of plasmids to generate KSHV-LPs: To generate polyvalent KSHV-LP vaccine candidates incorporating multiple KSHV proteins (gpK8.1, gB, gL and gH), two cDNAs were constructed and synthesized (Genewiz, South Plainfield, NJ). Each sequence included the gpK8.1 ectodomain (ED) fused to NDV fusion protein (F) transmembrane/cytoplasmic (TM/CT) domains (gpK8.1-F); the gB ED fused to NDV F TM/CT (gB-F), full-length wild-type gL without an F fusion (WTgL), and the gH ED fused to NDV F TM/CT (gH-F). In one cDNA, each NDV F TM/CT domain also contained heptad region 2; in the other cDNA, it did not (+/−HR2). To express this complex in its native form, unique 2A linker sequences (18 amino acids long) from picorna virus (41) were interspersed between individual glycoprotein cDNAs. See Table 1.

TABLE 1

2A Linker Sequences

| 2A Position | Nucleotide Sequence | Amino Acid Sequence |
|---|---|---|
| gpK8.1-gB | GCTACTAACTTCAGCCTGCTGAAGCAGGCT GGAGACGTGGAGGAGAACCCTGGACCT (SEQ ID NO: 6) | ATNFSLLKQAGDV EENPGP (SEQ ID NO: 7) |
| gB-gL | GCGACTAACTTCTCATTGTTGAAACAGGCA GGAGATGTCGAAGAGAACCCTGGTCCA (SEQ ID NO: 8) | ATNFSLLKQAGDV EENPGP (SEQ ID NO: 9) |
| gL-gH | GCAACGAATTTCTCCCTTCTAAAGCAAGCC GGTGACGTGGAGGAGAATCCCGGACCC (SEQ ID NO: 10) | ATNFSLLKQAGDV EENPGP (SEQ ID NO: 11) |

As disclosed herein, use of 2A linkers resulted in a polycistronic plasmid with cleavage sites that allow gpK8.1-F, gB-F, WTgL, and gH-F to be processed independently after transcription, and released to natively incorporate on the VLP envelope. The two synthesized chimeric cDNAs (gpK8.1-F-2A-gB-F 2A-WTgL-2A-gH-F+/−HR2) cloned into a mammalian expression plasmid, pCAGGS. Plasmids encoding for full-length NDV NP and M cloned into a pCAGGS plasmid have been described. Sanger sequencing was used to verify the sequence fidelity of all synthesized and cloned constructs. All primer sequences used in the study are listed in Table 2.

TABLE 2

Primer Sequences

| Primer Name | Primer Sequence (5'-3') |
|---|---|
| Cloning Primers | |
| KSHV K8.1-Fc-His FWD | AAAAAGCGGCCGCGCCACCATGAGTTCCACACAGATTCG (SEQ ID NO: 12) |
| KSHV K8.1-Fc-His REV | AAAAAACTAGTGTAAAGATGGGTCCGTATTTCTGC (SEQ ID NO: 13) |
| KSHV gB-Fc-His FWD | AAAAAGCGGCCGCGCCACCATGACTCCCAGGTCTAGATTGG (SEQ ID NO: 14) |
| KSHV gB-Fc-His Rev | AAAAAACTAGTTTTAATAAAATTTATGAATCCGGTAAC (SEQ ID NO: 15) |
| KSHV gH-gL Gibson.FOR | TTCTCGAGGATCCGCGGCCGCGCCACCATGGGGATCTTTGCGCTATTTG (SEQ ID NO: 16) |
| KSHV gHgL Gibson.REV | GCATGTGTGAGTTTTGTCACTAGTTGCGCGTCTTCTATACATGCC (SEQ ID NO: 17) |
| Sequencing Primers | |
| FC-Hisseqprimer1 | GTCGAGGTCTCGACGGTATCG (SEQ ID NO: 18) |
| FC-Hisseqprimer2 | CTCTATAGGCACACCCCTTTGG (SEQ ID NO: 19) |
| FC-Hisseqprimer3 | CGCGCGCCACCAGACATAATAG (SEQ ID NO: 20) |
| FC-Hisseqprimer4 | GCTTTAATAAGATCTCTAG (SEQ ID NO: 21) |
| FC-Hisseqprimer5 | TGCTGGGCACGGTGGGCATG (SEQ ID NO: 22) |
| FC-Hisseqprimer6 | GGGTCTTTTCTGCAGAAGCTTG (SEQ ID NO: 23) |
| FC-Hisseqprimer7 | CTGACCAAGAACCAGGTCAGC (SEQ ID NO: 24) |
| FC-Hisseqprimer8 | GACGCTCAAGTCAGAGGTGGC (SEQ ID NO: 25) |
| FC-Hisseqprimer9 | CTCCCCGTCGTGTAGATAACTAC (SEQ ID NO: 26) |
| FC-Hisseqprimer10 | CAATATTATTGAAGCATTTATC (SEQ ID NO: 27) |
| FC-Hisseqprimer11 | TGCGTAAGGAGAAAATACCGC (SEQ ID NO: 28) |

Figure 5:
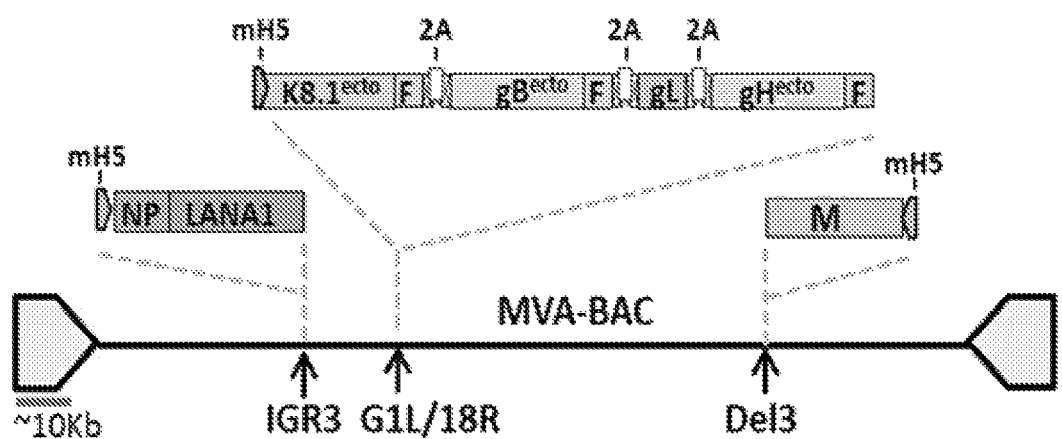
FIG. 5 shows the construction of various MVA vector constructs expressing multiple KSHV antigens.

Generation and production of MVA-KSHV-LPs: For MVA-KSHV-5Ag-VLP construct, vectors for gene insertion into the Deletion III site (Del3) (mH5-M), and the insertion site between the essential ORFs G1 L and 18R a 2A-linked polycistronic expressing transcript including the K8.1 ectodomain (ED) fused to NDV fusion protein (F) transmembrane/cytoplasmic (TM/CT) domains (K8.1-F); the gB ED fused to NDV F TM/CT (gB-F); and the gH ED fused to NDV F TM/CT (gH-F) without heptad region 2 (−HR2); and full-length wild-type gL (WTgL) between gB and gH, inserted into the MVABAC-TK can be transferred. Additionally, the IGR3 site inserted with NDV NP (28 amino acids) fused with partial LANA1 (937-1124 amino acids) protein of KSHV, as depicted in FIG. 5.

Transfection and generation of stable cells to produce KSHV-LPs: To generate gpK8.1-gB-gL-gH KSHV-LPs, 2 µg of pCAGGS-gpK8.1-F-2A-gB-F-2A-WTgL-2A-gH-F+/−HR2 plasmid was transiently transfected into CHO or HEK-293 cells using linear polyethylenimine (PEI) transfection regent (ThermoFisher Scientific). After 48 hours, cells were stained with anti-K8.1 (clone 4A4) primary antibody for 30 minutes, washed three times with 1× phosphate buffered saline (PBS), and stained with goat anti-mouse secondary antibody conjugated to AF488. Stained cells were washed three times and analyzed using FACS to detect surface expression of gpK8.1 on the cells. Untransfected and unstained CHO or HEK-293 cells served as negative controls for FACS analysis. Upon confirmation of gpK8.1 expression in both CHO and HEK-293 cells, only CHO cells were then co-transfected as above with individual pCAGGS-gpK8.1-F-2A-gB-F-2A-WTgL-2A-gH-F+/−HR2 and pCl-puro plasmids, followed by 5 µg/µl of puromycin selection 48 hours post-transfection, to generate stable cells expressing the four glycoproteins. Stable CHO cells resistant to puromycin selection were pooled and stained with primary anti-gpK8.1 mAb (4A4), followed by secondary goat Fab-2 anti-mouse IgG (H+L) conjugated to AF488 and sorted five times to generate a colony of CHO cells expressing mainly gpK8.1-gB-WTgL-gH+/−HR2 (~50% anti-K8.1-AF488 positive). Stable cells were then co-transfected with equal amounts of both pCAGGS-NDV M and pCAGGS-NDV NP plasmids to produce gpK8.1-gB-gH/gL+/−HR2 VLPs (KSHV-LPs). Additional VLPs were also produced by transiently co-transfecting CHO or HEK-293 cells with pCAGGS encoding for NDV M, NDV NP, and polycistronic gpK8.1-F-2A-gB-F-2A-WTgL-2A-gH-F+/−HR2 plasmids.

Purification and characterization of KSHV-LPs: Supernatants from stable cells releasing KSHV-LPs were collected 24-120 hours post-transfection, and combined, then cell debris was removed by centrifugation at 3,724×g (Corning 500 ml centrifuge tubes, SX4750 rotor) for 15 minutes at 4° C. To pellet the KSHV-LPs, the resultant supernatant was centrifuged in a type 19 fixed angle aluminum rotor (Beckman Coulter, Brea, CA) at 9,846×g at 4° C. for 12 hours. The resultant pellet was re-suspended in 4 ml TNE buffer (25 mM Tris-HCl, pH 7.4, 150 mM NaCl, and 5 mM EDTA) and layered on a discontinuous sucrose gradient composed of 2 ml of 65% sucrose and 4 ml of 20% sucrose. The gradients were centrifuged at 42,953×g at 4° C. in an SW 40Ti rotor (Beckman Coulter, Brea, CA) for 12 hours. The fluffy layers at the 20-65% interface containing the KSHV-LPs were collected, mixed with two volumes of 80% sucrose and sandwiched between 1 ml of 80% sucrose (at the bottom of the tube) and 3.5 ml of 50% sucrose (on top); 2 ml of 10% sucrose was then laid on top. The mixture was centrifuged for 12 hours at 91,349×g in a type SW 40Ti rotor at 4° C. The resultant VLP fluffy layer was collected, re-suspended in 1×TNE and pelleted at 91,349×g in an SW 40Ti rotor (Beckman) at 4° C. for 1 hour. The resultant pellet was then re-suspended in TNE, total protein was quantified using BCA assay (Pierce, Rockford, IL) and purified VLPs were stored at −20° C. or 4° C. until further use.

Construction, purification and characterization of KSHV gpK8.1, gB and gH/gL proteins: To construct KSHV gpK8.1, gB, and gH/gL Fc-6×His tagged plasmids, the coding sequence for each protein ED was PCR-amplified with gene-specific primers (Table 1) from previously described pCAGGS gpK8.1, pCAGGS gB, and pCAGGS gH/gL constructs. The upstream (5') and downstream (3') primers contained NotI and SpeI enzyme restriction sites (gpK8.1 and gB), respectively, or Gibson assembly primers (gH/gL), which were used to subclone the PCR products into the Cntn1-Fc-His plasmid from Addgene plasmid #72065 (Watertwon, MA), a gift from Dr. W. Wojtowicz, Stanford University, Palo Alto, CA.

Fc-6×His-tagged recombinant KSHV gpK8.1, gB and gH/gL proteins were expressed via transient transfection of HEK-293 6E using linear PEI transfection reagent. Cells were seeded a day before transfection at 800,000 cells/ml in a 250 ml of media in a 1-liter Erlenmeyer flask, the following day 200 μg of plasmid DNA and linear PEI at a 1:5 DNA:PEI ratio were added to 9 ml Opti-MEM (ThermoFisher Scientific), mixed gently, incubated for exactly 20 minutes at room temperature and added dropwise onto cells to make a final volume of 250 ml. Culture media was harvested six days post-transfection by centrifugation and filtration through a 22 μM filter. The Fc-6×His-tagged KSHV proteins in the media were purified using Protein A spin columns (Takara Bio, Kusatsu, Shiga, Japan), buffer exchanged and concentrated into PBS using Amicon Ultra 15 centrifugal filter units (MilliporeSigma) and then quantified using a nanodrop spectrophotometer (ThermoFisher Scientific).

Generation and identification of KSHV-glycoprotein-specific monoclonal antibodies: Monoclonal antibodies specific to KSHV gpK8.1, and gH/gL were generated using standard techniques (44). Briefly, to generate, identify, and characterize KSHV-glycoprotein-specific mAbs, four wild-type BALB/c mice were immunized intraperitoneally with 200 μl containing 100 μg of complete Freund's adjuvant (MilliporeSigma F5881) mixed with 50 μg of purified UV-inactivated rKSHV-eGFP.219 (UV-KSHV) resuspended in TNE buffer. The animals were boosted five times with 200 μl containing 100 μg of incomplete Freund's adjuvant (MilliporeSigma F5506) and 25 μg of UV-KSHV resuspended in TNE buffer every two weeks. Once optimal antibody response to gpK8.1 and gH/gL in sera was confirmed using ELISA, a sixth booster immunization was provided intravenously with 200 μl containing 25 μg of UV-KSHV resuspended in TNE. Boosted mice were sacrificed, and splenocytes were isolated and fused with a mouse myeloma cell line (P3X63Ag8.653) to generate murine hybridomas, using a standard polyethylene glycol (PEG) method, and cultured as described (44). On Day 7 post-fusion, cells were fed with 100 μl hypoxanthine-aminopterin-thymidine medium media per well. On Days 10-14, growing hybridomas were resuspended and cells reseeded in duplicate 96-well plates and allowed to grow for three days. Supernatants from one of the duplicate 96-well plate hybridoma plates were collected to perform indirect ELISA with purified KSHV proteins (gpK8.1 or gH/gL) to identify hybridoma colonies that secreted murine IgG antibodies specific to KSHV gpK8.1 or gH/gL. Positive hybridomas were expanded from the second 96-well plate and screened by performing confirmatory ELISA, FACS and immunoblot. Identified antibodies were expanded and bulk purified through protein A spin columns and stored at −20° C. for subsequent assays.

Sodium dodecyl sulphate polyacrylamide gel electrophoresis (SDS-PAGE), Coomassie staining and immunoblotting: Cells and KSHV-LPs were lysed in RIPA buffer (10 mM Tris-HCL, pH 8.0, 1 mM EDTA, 140 mM NaCl, 0.1 Triton X-100, protease inhibitor cocktail) (MilliporeSigma). The lysed suspensions were vigorously vortexed, incubated on ice for 30 minutes, and then centrifuged at 15,871×g for 10 minutes at 4° C. in a benchtop centrifuge. The supernatants were collected and total protein was quantified using BCA assay. A known quantity of protein was loaded onto a 4-12% polyacrylamide gel for protein separation using 1×MES SDS running buffer (ThermoFisher Scientific), then either the gel was stained with Coomassie blue or proteins were transferred from the gel to a polyvinylidene fluoride membrane using iBlot (ThermoFisher Scientific) for immunoblot analysis. Immunoblot analyses for proteins (i.e., gpK8.1, gB, gH/gL, and NDV-NP) were performed by blocking the membrane with 3% bovine serum albumin (MilliporeSigma) in Tris-buffered saline (TBS) for 1 hour at room temperature, followed by detection with relevant specific primary and secondary antibodies as described (30). 2A protein peptide and Fc-tagged proteins were detected using their respective antibodies following antibody manufacturers' protocols.

Transmission electron microscopy (TEM): To assess the composition of KSHV-LPs compared to wild-type KSHV, morphological examination was conducted using TEM. KSHV-LPs were purified as described above and rKSHV-eGFP.219 virus was harvested and purified from iSLK KSHV-eGFP.219 cells as described. Purified KSHV-LPs+/−HR2 and rKSHV-eGFP.219 were fixed in 4% paraformaldehyde in preparation for TEM. Specimens were absorbed to glow-discharged, carbon-coated, 200-mesh EM grids. Samples were prepared by conventional negative staining with 1% (w/v) uranyl acetate. EM images were collected with an FEI Tecnai 12 TEM (ThermoFisher Scientific) equipped with a LaB6 filament and operated at an acceleration voltage of 120 kV. Images were recorded with a Gatan 2×2 k CCD camera (Gatan, Inc., Pleasanton, CA, USA) at a magnification of 21,000× and a defocus value of ~1.5 μm.

Immunization of wild-type New Zealand white rabbits and collection and processing of serum samples: Female and male wild-type New Zealand white rabbits 8-10 weeks old were immunized subcutaneously three times on Days 0, 21, and 42 with 50 μg total protein of purified individual KSHV-LPs+/−HR2 (n=6 each group) in 0.5 ml TNE buffer adsorbed to 500 μg aluminum hydroxide (alum) mixed with 50 μg of monophosphoryl lipid A from *Salmonella enterica* serotype Minnesota Re595 (MPL) as adjuvants; alum/MPL-adjuvanted UV-KSHV (n=6) or alum/MPL-adjuvanted TNE (n=6) served as positive and negative controls, respectively. Rabbits were bled before immunization (pre-bleed baseline) and on Days 14, 35, 49, 70, and 90 (terminal bleed).

Following collection of blood, whole blood was allowed to coagulate for 2 hours at room temperature, then incubated overnight at 4° C. To process whole blood into serum, the whole blood was centrifuged at 2,348×g for 15 minutes at 4° C. The serum was transferred into a clean tube and centrifuged again at 2,348×g for 5 minutes at 4° C. The final serum was poured into a vial and then crimp-sealed. The vial of serum was then stored at −80° C. until being aliquoted for subsequent experiments.

Measurement of anti-gpK8.1-, gB- and gH/gL-specific antibody titers in sera from immunized rabbits using ELISA: Using sera collected from wild-type New Zealand white rabbits, antibodies titers were assessed by ELISA, using individual purified glycoproteins as the target. Briefly, wells of 96-well microtiter plates were coated with 0.5 μg of individual purified glycoprotein EDs (KSHV gpK8.1, gB, or gH/gL) in 50 μl of PBS buffer at 4° C. overnight, and blocked with 3% BSA in 1×PBS and 0.1% tween for 1 hour at room temperature. Serially diluted sera (1:100, 1:300, 1:900, 1:2,700 and 1:8,100 in PBS) were added to the protein coated plates in quadruplicates and incubated for 2 hours at room temperature. Plates were washed three times and antibody binding was detected using HRP-labeled goat anti-rabbit IgG secondary antibodies for 1 hour at room temperature. Plates were washed three times, the substrate tetramethylbenzidine (ThermoFisher Scientific) was added for 20 minutes at room temperature, then the reaction was stopped with 1×KPL ABTS peroxidase stop solution (Sera Care, Milford, MA). To determine antibody titer, optical density was read at 405 nm using an ELISA reader, FilterMax F3 (Molecular Devices, San Jose). The highest antibody dilution yielding an $OD_{405}$ two times higher than that of TNE-treated rabbits (negative control) was designated as the endpoint titer.

Purification of IgG antibodies from rabbit sera and determination of anti-gpK8.1-, gB-, and gH/gL-specific antibodies: Purification of IgG antibodies was conducted by pooling Day 49 sera (highest antibody titer) from immunized rabbits (n=6) from each of the four treatment/control groups. Pooled sera were diluted 1:10 in equilibration/binding/wash buffer (1.5M glycine, 3M NaCl, pH 9.0), added to protein A columns, and centrifuged at 2,000×g for 3 minutes at room temperature. Centrifugation flow-through was discarded and the columns were washed with 6 ml of wash buffer, followed by 1 ml of elution buffer (0.2 M Glycine, pH 2.5); samples were eluted into new collection tubes containing 100 μl neutralization buffer (1 M Tris/HCl, pH 9.0) by centrifugation at 2,000×g for 3 minutes at room temperature. Purified IgGs were buffer exchanged and concentrated in PBS, protein concentration was determined using nanodrop, and IgGs were separated using SDS-PAGE and stained with Coomassie to determine purity. ELISA was used to determine the titers of anti-gpK8.1-, gB-, and gH/gL-specific antibodies from purified IgGs at different concentrations (25, 12.5, 6.25, 3.125, and 1.56 μg/ml). IgGs were stored at 4° C. until use in subsequent experiments.

In vitro neutralization assay: In vitro neutralization was performed using different cell types of human origin, namely epithelial (HEK-293), fibroblast (HFF-1), endothelial (HUVEC), and B (MC116) cells. To conduct neutralization, rKSHV-eGFP.219 was first tittered in individual cell types. Briefly, each individual cell line was seeded in quadruplicate at a density of $5\times10^5$ in 48-well-plates and cultured overnight. The individual cell lines were then incubated with 5, 10, 20, 30, or 50 μl of the purified virus in a total volume of 100 μl of virus plus serum-free media for 24 hours at 37° C. Infected cells (eGFP-positive) were quantified using FACS by acquiring a total of 10,000 events and analyzed using FlowJo Software (FlowJo LLC, Ashland, Oregon) as described.

Upon determination of virus titer, cells were seeded as above. Purified IgGs were serially diluted in serum-free media to 12.5, 25, 50, or 100 μg/ml and incubated for 1 hour at 37° C. with a known quantity of the virus that yielded 20-30% infectivity in the respective cell type used. The mixture of purified IgGs and virus were then added to the seeded cells and incubated for 2 hours at 37° C. for adherent cells or spinoculated at 233×g for 30 minutes at room temperature for B cells (MC116). Infected cells were washed three times in 1×PBS to remove excess IgGs and circulating viruses, and complete media were added and cells were incubated for 24 hours at 37° C. The number of eGFP-positive cells (i.e., rKSHV-eGFP.219-infected cells) was enumerated using FACS by acquiring 10,000 events. All dilutions were performed in quadruplicate and assays repeated at least once.

Statistical analysis: Statistical analyses were performed using GraphPad Prism 8 Software (GraphPad Software, San Diego, CA, USA). Multiple comparisons between groups were calculated using Kruskal-Wallis, whereas differences between groups were computed using Dunn's post hoc test and Mann-Whitney U test. All statistical tests were two-tailed, and a p-value equal to or lower than 0.05 was considered significant. $IC_{50}$ (μg/ml) values were calculated from neutralization data of KSHV.219 by purified IgGs in HEK-293, HFF-1, HUVEC and MC116 cells using nonlinear, dose-response regression analysis.

Example 2: Construction, Purification, and Characterization of KSHV-LPs that Incorporate Four KSHV Proteins as Vaccine Candidates It was previously demonstrated that the NDV-LP platform could be used to generate iKSHV-LPs incorporating a single surface envelope glycoprotein (gpK8.1 or gB) or two-glycoprotein complex (gH/gL) (30). In this study, two versions of a single polycistronic plasmid encoding sequences for four glycoproteins, designated pCAGGS-gpK8.1-F-2A-gB-F-2A-WTgL-2A-gH-F+/−HR2, as reagents for making multivalent KSHV-LPs (FIG. 1A). In these plasmid constructs, the EDs of three KSHV glycoproteins (gpK8.1, gB, and gH) were fused to the structural protein NDV F with or without HR2; the NDV F HR2 domain was used to support trimerization of the proteins and help increase the number of immunogens per VLP. Full-length wild-type KSHV gL was incorporated because it does not have a transmembrane domain and depends on gH for its transport to the surface of the virion. All four glycoproteins were interspersed with a picornavirus 2A self-cleaving peptide for efficient expression and cleavage under a single cytomegalovirus promoter.

Figure 1B:
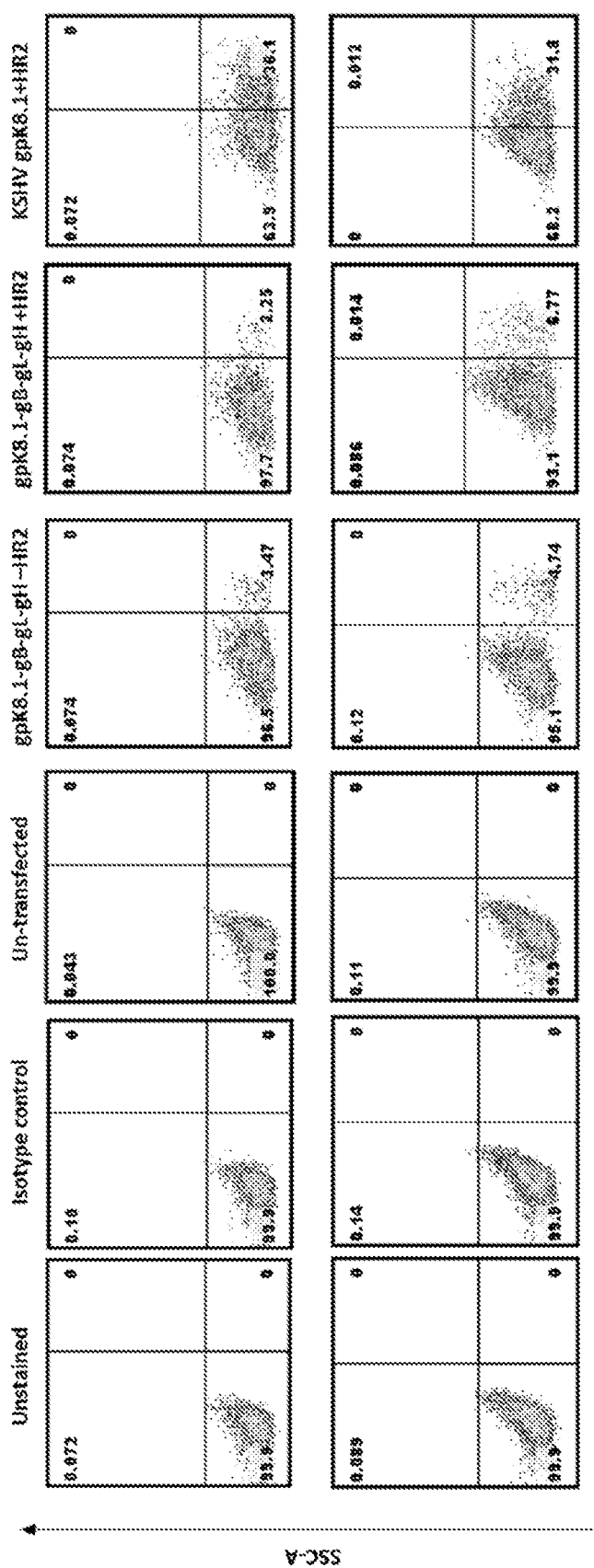

To confirm plasmid DNA transfection efficiency and expression of various glycoproteins from the polycistronic plasmids, each plasmid was transiently transfected into CHO or HEK-293 cells, two epithelial cell lines widely used in most laboratories for protein expression. To confirm the expression of proteins on the cell surface, transfected cells were stained with anti-K8.1 primary antibody, followed by mouse secondary antibody conjugated to AF 488, then FACS was used to detect surface expression of gpK8.1. The previously constructed pCAGGS-K8.1-F+HR2 plasmid was used as a positive control for gpK8.1 expression and untransfected cells and unstained transfected cells were used as negative controls. Transfected CHO and HEK-293 cells expressed gpK8.1 (FIG. 1B). However, the total number of transfected cells expressing gpK8.1 was low in both HEK-293 and CHO cells transfected with the polycistronic plasmids compared to cells transfected with the plasmid encoding for a single protein. For example, in CHO cells transfected with gpK8.1-F-2A-gB-F2A-WTgL-2A-gH-F −HR2 or +HR2, gpK8.1 expression was found to be 4.74% and 6.77%, respectively, compared to 31.8% in CHO cells transfected with pCAGGS-gpK8.1-F+HR2. This occurred despite the optimization of transfection efficiency using various ratios of DNA:PEI or other transfection reagents (data not shown), and was probably due to the large cDNAs cloned into the plasmids.

To overcome poor transfection efficiency and improve KSHV-LP production for full characterization and immunogenicity testing, CHO cells stably expressing each multicistronic plasmid were established. Only CHO cells were used because over two-thirds of recombinant therapeutic agents on the market are generated in CHO cell lines and because no adventitious human pathogen has been reported for CHO cells. CHO cells were co-transfected with pCAGGS-gpK8.1-F-2A-gB-F-2A-WTgL-2A-gH-F+/−HR2 and pCI-puro. The transfected cells were cultured in 5 μg/ml of puromycin, resistant cells were stained with anti-K8.1-AF488 antibody and FACS sorted five times to enrich for cells expressing gpK8.1 (FIG. 2A). Selection was based on gpK8.1 due to a lack of well-validated monoclonal antibodies against the other KSHV glycoproteins at the time of making the stable cell lines.

Figure 2C:
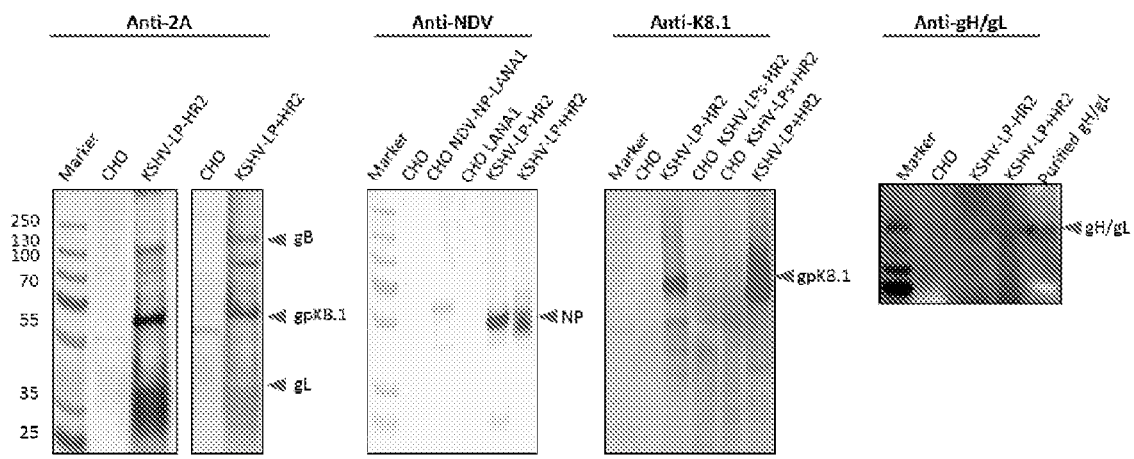
Figure 2D:
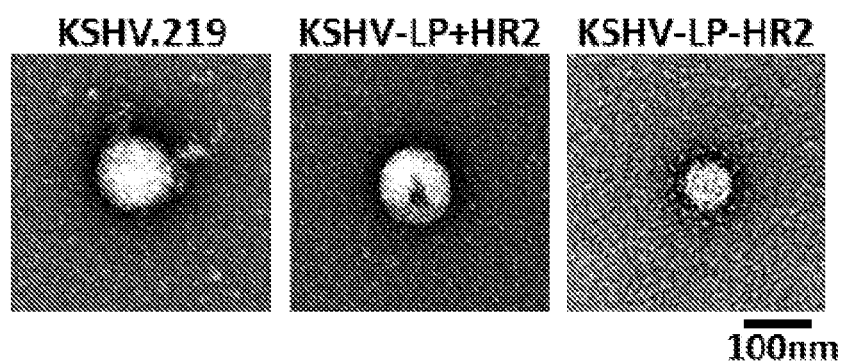

To produce KSHV-LPs, enriched stable cells were co-transfected with both pCAGGS-NDV M and pCAGGS-NDV NP, and then supernatants from the transfected cells were collected daily from 24 hours post-transfection until 120 hours post-transfection. KSHV-LPs were purified from the supernatants using sucrose-gradient sedimentation, followed by floatation gradients (FIG. 2B), then fully characterized for their composition and structure as described (30). In brief, immunoblotting was used to confirm that all four KSHV glycoprotein subunits were incorporated into the KSHV-LPs+/−HR2. Rabbit polyclonal anti-2A and anti-NDV and mouse monoclonal anti-K8.1 and anti-gH/gL antibodies were used to show that all components (i.e., KSHV glycoproteins and NDV structural proteins) were incorporated and packaged into VLPs (FIG. 2C). The use of anti-2A also detected unidentified proteins of higher molecular weights in VLPs; whether these are uncleaved proteins incorporated in the VLPs or cell debris in the purified VLP fraction remains to be elucidated. Because the 2A sequence between WTgL and gH-F is cleaved and remains with WTgL, it is not possible to use the anti-2A antibody to detect gH. Thus, to further confirm the specificity of the K8.1 protein bands and also detect gH/gL protein complex, specific monoclonal antibodies anti-gpK8.1 (41E7), and anti-gH/gL (57C12) generated in the laboratory were used to detect the individual proteins (FIG. 2C). No commercially available KSHV anti-gB antibody can be used to prove the presence of gB in the KSHV-LPs. However, the molecular weight identified for each KSHV subunit agreed with published data, providing strong evidence that KSHV-LPs generated from a polycistronic plasmid are faithful to the composition of the subunits. Electron microscopy was used to confirm that the size, shape, and morphology of KSHV-LPs were similar to rKSHV-eGFP.219 virus: the VLP diameters were ~100 nm, with a spherical shape and spike-like structures, resembling glycoproteins incorporated into the virions (FIG. 2D).

Figure 3A:
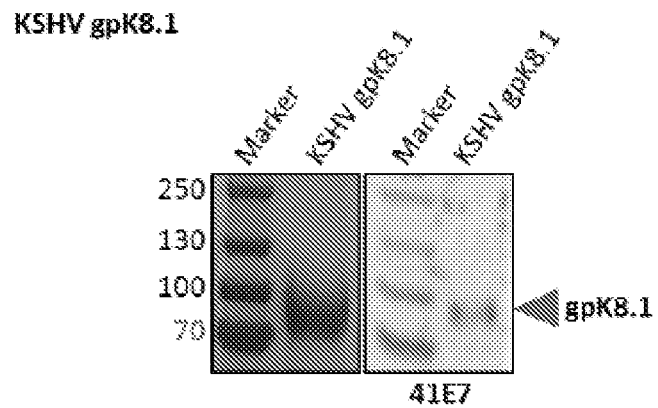
FIGS. 3A-3C show KSHV-glycoprotein-specific IgG titers in immunized New Zealand white rabbits.
Figure 3A:
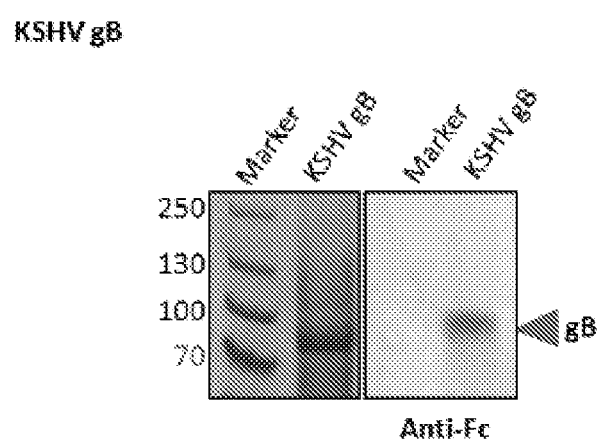
Figure 3A:
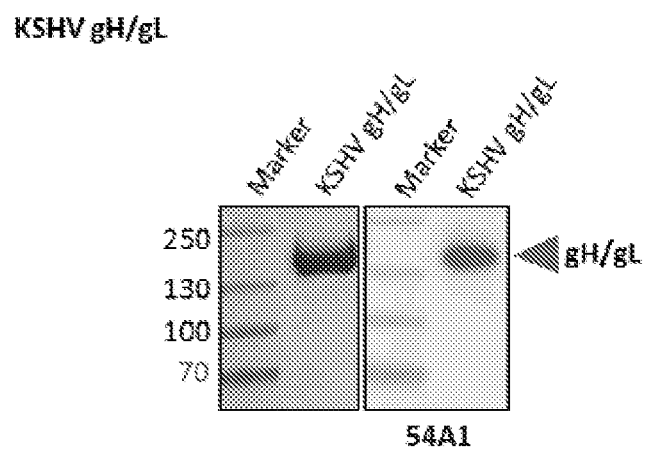

Example 3: Rabbits Immunized with KSHV-LPs+/−HR2 Elicited High Titer KSHV-Glycoprotein-Specific Antibody Responses The results of the previous experiments demonstrated that mice immunized singly or with combinations of KSHV-LPs expressing gpK8.1, gB, or gH/gL without adjuvant were able to generate robust antibody responses and stimulate KSHV glycoprotein-specific immune recall upon boosting (30). To demonstrate the ability of the multivalent KSHV-LPs disclosed herein to induce KSHV subunit-specific antibody responses, wild-type New Zealand white rabbits were immunized with alum/MPL-adjuvanted KHSV-LPs+/−HR2, and then ELISA was used to determine antibody titers and kinetics over time. Selection of the alum and MPL formulation was based on AS04, an adjuvant licensed for human use that is currently being used in two licensed VLP-based vaccines, the human papillomavirus vaccine Cervarix® (GlaxoSmithKline) and the hepatitis B vaccine FENDrix® (GlaxoSmithKline). Because there is no good standard for measuring IgGs against KSHV infection in human or immunized animals due to the inconsistent detection of KSHV-specific protein IgGs in KSHV-infected individuals, purified proteins were used as binding targets for use in ELISA as described (45). Taking advantage of the constructed plasmids individually encoding for soluble gpK8.1, gB, or gH/gL proteins, each plasmid was transfected into HEK-293 6E cells (which enabled high-yield production of post-translationally modified recombinant proteins in serum-free media), supernatants from the transfected cells were collected, clarified and purified through protein A columns. The purified proteins were concentrated and quantified and their authenticity was confirmed by both Coomassie blue staining and immunoblot using specific anti-gpK8.1 or anti-gH/gL monoclonal antibodies or polyclonal anti-human Fc for gB (FIG. 3A).

Figure 3B:
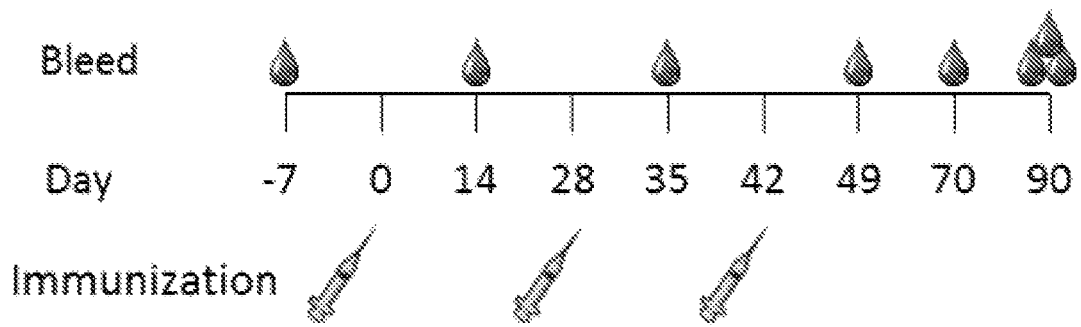
Figure 3C:
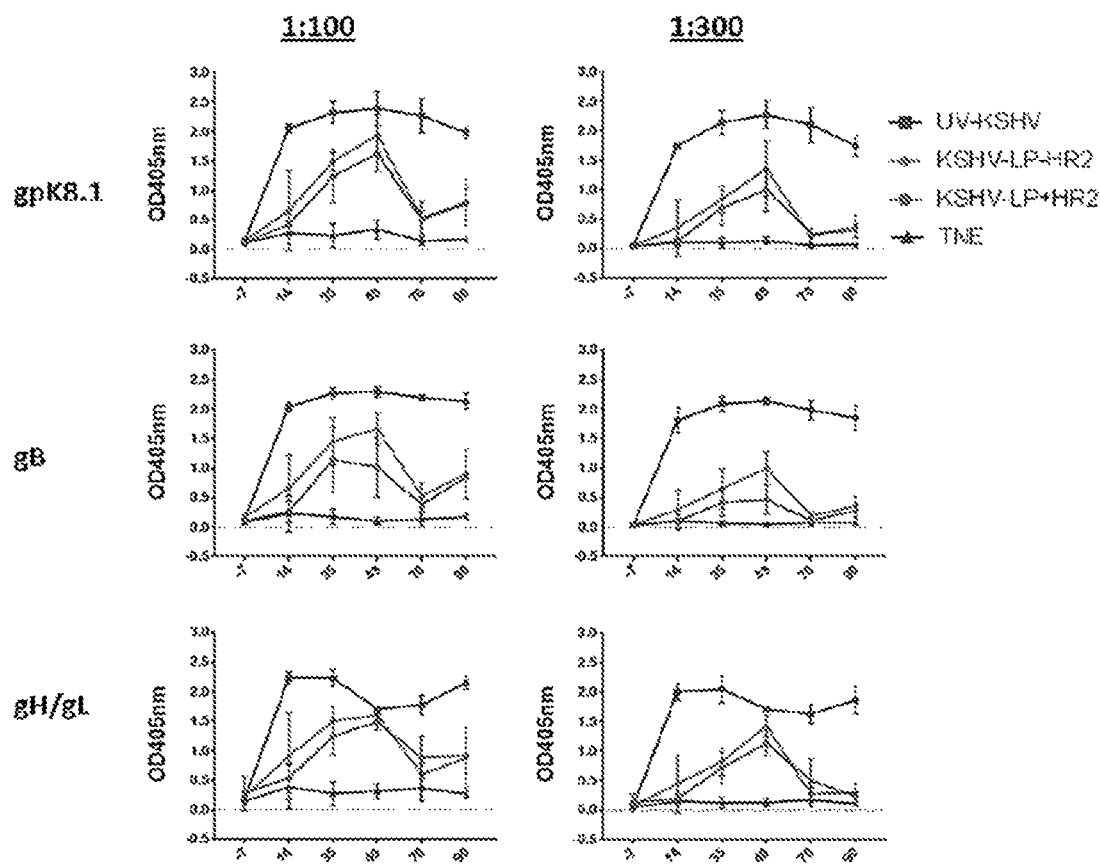

To characterize antibody immune responses, 8-10-week-old wild-type New Zealand white rabbits were immunized subcutaneously three times (Days 0, 21, and 42) with 50 μg of purified KSHV-LPs+/−HR2. Each of the KSHV-LPs was suspended in 0.5 ml TNE buffer adsorbed to 500 μg alum and 50 μg MPL. The alum and MPL adjuvants were used to improve humoral and cellular immunogenicity. Rabbits immunized with 50 µg of purified UV-KSHV or TNE, adjuvanted with alum/MPL, served as positive and negative controls, respectively. To obtain enough sera to support complete characterization of antibody responses, 6 rabbits per group were used. To assess short- and long-term antibody responses, rabbits were bled to obtain sera seven days before the first immunization (pre-bleed) and on Days 14, 28, 35, 49, 70, and 90 (terminal bleed) (FIG. 3B). ELISA was used to determine KSHV-glycoprotein-specific antibody titers from each individual animal over time using the purified proteins described above as the binding targets. All rabbits immunized with KSHV-LPs+/–HR2 or UV-KSHV generated KSHV-glycoprotein-specific IgG antibody responses that increased following booster immunizations, compared to TNE-immunized rabbits or pre-bleeds (negative controls) (FIG. 3C). The increase in KSHV glycoprotein-specific antibody response peaked by Day 49, after the second booster immunization. There was no difference in the titers of the glycoproteins (K8.1, gB, or gH/gL) between rabbits immunized with KSHV-LPs+HR2 or –HR2. Compared to either KSHV-LP+/–HR2, UV-KSHV immunization elicited significantly higher titers of KSHV-glycoprotein-specific antibodies, which remained high through Day 90. In contrast, the antibody titers from animals immunized with either KSHV-LP+/–HR2 dropped by Day 70 (Mann-Whitney test; gpK8.1 Day 49 vs Day 70: KSHV-LPs –HR2 p=0.0022, KSHV-LPs+HR2 p=0.0022; gB Day 49 vs Day 70: KSHV-LPs –HR2 p=0.0022, KSHV-LPs+HR2 p=0.0022; gH/gL Day 49 vs Day 70: KSHV-LPs –HR2 p=0.0043, KSHV-LPs+HR2 p=0.0303), suggesting that long-term antibody responses in KSHV-LP+/–HR2-immunized rabbits were weaker than those of UV-KSHV immunized rabbits.

Example 4: KSHV-LPs+/–HR2 Elicit Robust Neutralizing Antibodies that Prevent rKSHV-eGFP.219 Infection in Diverse Cell Types To measure the ability of KSHV-glycoprotein-specific polyclonal antibodies in sera from rabbits immunized with multivalent KSHV-LPs to neutralize viral infection and to reduce the previously observed serum effect, IgGs from Day 49 samples (highest titers) were pooled and purified, and then KSHV-glycoprotein-specific IgGs were quantified using ELISA (FIG. 4A). Similar to unpurified sera, titers for gpK8.1-, gB-, and gH/gL-specific IgGs were significantly higher in rabbits immunized with purified KSHV-LPs+/–HR2 compared to TNE (negative control) using a non-parametric Kruskal-Wallis test (gpK8.1, p=0.0003; gB, p=0.0002; gH/gL, p=0.0012). KSHV-specific IgG titers were higher in rabbits immunized with KSHV-LPs–HR2 than KSHV-LPs+HR2; for example, at 25 µg/ml, gpK8.1, gB and gH/gL IgG titers were 4-fold higher. However, titers were highest in rabbits immunized with UV-KSHV. For example, at 25 µg/ml, gpK8.1, gB and gH/gL IgG titers in UV-KSHV were 3-fold and 10-fold higher than in KSHV-LPs–HR2 and KSHV-LPs+HR2 IgG-purified samples, respectively (FIG. 4A).

Figure 4B:
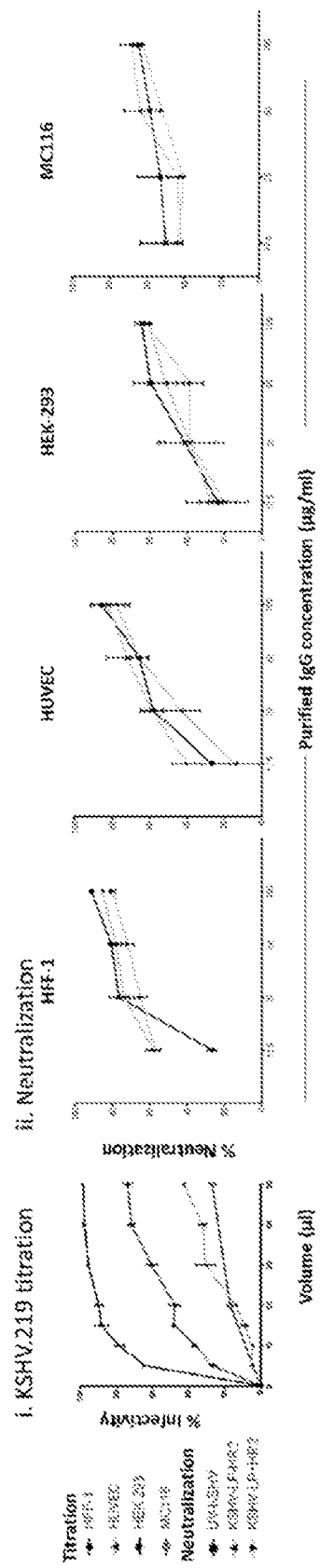

After confirming the presence and titers of KSHV-glycoprotein-specific antibodies in the purified sera, neutralization activity assays were performed in diverse cell types that represented most of the cell types permissive to KSHV infection in vivo. First, purified rKSHV-eGFP.219 was titrated in four permissive cell types of human origin to determine volumes that ensured >20% rKSHV-eGFP.219 infectivity for in vitro neutralization (FIG. 4B, Panel i). To conduct in vitro neutralization assays, serially diluted purified IgGs (12.5, 25, 50, or 100 µg/ml) were incubated with rKSHV-eGFP.219. The percentage of eGFP+ cells (i.e., KSHV-infected cells) was measured using FACS and an effective neutralization titer was defined as 50% inhibition of infection, after normalization to control IgG samples from TNE-immunized rabbits. When rKSHV-eGFP.219 virus was pre-incubated with serially diluted concentrations of total purified IgG antibodies (12.5, 25, 50, or 100 µg/ml) from TNE-immunized rabbits (negative control), all concentrations achieved ~8% neutralizing activity (serum effect) in a non-dose-dependent manner in HEK-293 cells (data not shown). Thus, 8% was used as the normalization percentage to account for the serum effect in all subsequent neutralization assays. In contrast, rKSHV-eGFP.219 pre-incubated with serially diluted concentrations of pooled purified IgGs from rabbits immunized with KSHV-LPs+/–HR2 or UV-KSHV resulted in a dose-dependent reduction of KSHV infection in an endothelial cell line (HUVEC), foreskin fibroblast cell line (HFF-1), and B cell line (MC116) (FIG. 4B, Panel ii). Purified IgGs from both groups of KSHV-LP+/–HR2-immunized rabbits blocked rKSHV-eGFP.219 infection in vitro in all cell types tested (FIG. 4B, Panel ii). Interestingly, despite UV-KSHV-immunized rabbits having higher titers of KSHV-glycoprotein-specific IgGs than KSHV-LP-immunized rabbits (FIG. 4A), there were no statistical differences in the neutralizing antibody activities between them in all cell lines tested (FIG. 4B). At the highest dilution analyzed (100 µg/ml), UV-KSHV and both KSHV-LPs+/–HR2 neutralized KSHV infection by 60-90% in all cell types tested (FIG. 4B, Panel ii). Importantly, even at the lowest concentration, IgGs from any of the vaccine candidates neutralized KSHV infection by 12-55%, in all cell types tested, with the highest neutralization activity being observed in HFF-1 cells. The calculated IC50 (Table 3) varied between cell lines and vaccine candidates: UV-KSHV, 14.07-28.89 µg/ml, KSHV-LPs –HR2, 26.56-37.97 µg/ml, and KSHV-LPs+HR2, 29.57-49.64 µg/ml. The results confirmed that a select group of KSHV glycoproteins incorporated on the surface of VLPs, and administered with appropriate adjuvants, can stimulate neutralizing antibodies that block KSHV infection of diverse cell types in vitro.

TABLE 3

| | $IC_{50}$ (µg/ml) | | |
|---|---|---|---|
| Cell-line | UV-KSHV | KSHV-LPs – HR2 | KSHV-LPS + HR2 |
| HEK-293 | 27.36 | 33.49 | 39.9 |
| HFF-1 | 21.41 | 26.56 | 36.24 |
| HUVEC | 28.89 | 28.2 | 29.57 |
| MC116 | 14.07 | 37.97 | 49.64 |

REFERENCES

1. Bray F, Ferlay J, Soerjomataram I, Siegel R L, Torre L A, Jemal A. Global cancer statistics 2018: GLOBOCAN estimates of incidence and mortality worldwide for 36 cancers in 185 countries. CA Cancer J Clin. 2018.
2. Mesri E A, Cesarman E, Boshoff C. Kaposi's sarcoma and its associated herpesvirus. Nature reviews Cancer. 2010; 10(10):707-19.
3. Cesarman E, Chang Y, Moore P S, Said J W, Knowles D M. Kaposi's sarcoma-associated herpesvirus-like DNA sequences in AIDS-related body-cavity-based lymphomas. The New England journal of medicine. 1995; 332 (18):1186-91.

4. Uldrick T S, Wang V, O'Mahony D, Aleman K, Wyvill K M, Marshall V, et al. An interleukin-6-related systemic inflammatory syndrome in patients co-infected with Kaposi sarcoma-associated herpesvirus and HIV but without Multicentric Castleman disease. Clinical Infectious Diseases. 2010; 51(3):350-8.
5. Soulier J, Grollet L, Oksenhendler E, Cacoub P, Cazals-Hatem D, Babinet P, et al. Kaposi's sarcoma-associated herpesvirus-like DNA sequences in multicentric Castleman's disease. Blood. 1995; 86(4):1276-80.
6. Wabinga H R, Parkin D M, Wabwire-Mangen F, Mugerwa J W. Cancer in Kampala, Uganda, in 1989-91: changes in incidence in the era of AIDS. Int J Cancer. 1993; 54(1): 26-36.
7. Wu T T, Qian J, Ang J, Sun R. Vaccine prospect of Kaposi sarcoma-associated herpesvirus. Curr Opin Virol. 2012; 2(4):482-8.
8. Jacobson L P, Jenkins F J, Springer G, Munoz A, Shah K V, Phair J, et al. Interaction of human immunodeficiency virus type 1 and human herpesvirus type 8 infections on the incidence of Kaposi's sarcoma. The Journal of infectious diseases. 2000; 181(6):1940-9.
9. Barozzi P, Bonini C, Potenza L, Masetti M, Cappelli G, Gruarin P, et al. Changes in the immune responses against human herpesvirus-8 in the disease course of posttransplant Kaposi sarcoma. Transplantation. 2008; 86(5):738-44.
10. Minhas V, Brayfield B P, Crabtree K L, Kankasa C, Mitchell C D, Wood C. Primary gamma-herpesviral infection in Zambian children. BMC Infect Dis. 2010; 10:115.
11. Minhas V, Crabtree K L, Chao A, M'Soka T J, Kankasa C, Bulterys M, et al. Early childhood infection by human herpesvirus 8 in Zambia and the role of human immunodeficiency virus type 1 coinfection in a highly endemic area. Am J Epidemiol. 2008; 168(3):311-20.
12. Gantt S, Orem J, Krantz E M, Morrow R A, Selke S, Huang M L, et al. Prospective Characterization of the Risk Factors for Transmission and Symptoms of Primary Human Herpesvirus Infections Among Ugandan Infants. The Journal of infectious diseases. 2016; 214(1):36-44.
13. Koelle D M, Huang M L, Chandran B, Vieira J, Piepkorn M, Corey L. Frequent detection of Kaposi's sarcoma-associated herpesvirus (human herpesvirus 8) DNA in saliva of human immunodeficiency virus-infected men: clinical and immunologic correlates. The Journal of infectious diseases. 1997; 176(1):94-102.
14. Webster-Cyriaque J, Edwards R H, Quinlivan E B, Patton L, Wohl D, Raab-Traub N. Epstein-Barr virus and human herpesvirus 8 prevalence in human immunodeficiency virus-associated oral mucosal lesions. The Journal of infectious diseases. 1997,175(6):1324-32.
15. Dittmer D P, Damania B. Kaposi sarcoma-associated herpesvirus: immunobiology, oncogenesis, and therapy. J Clin Invest. 2016; 126(9):3165-75.
16. Bechtel J T, Winant R C, Ganem D. Host and viral proteins in the virion of Kaposi's sarcoma-associated herpesvirus. Journal of virology. 2005; 79(8):4952-64.
17. Zhu F X, Chong J M, Wu L, Yuan Y. Virion proteins of Kaposi's sarcoma-associated herpesvirus. Journal of virology. 2005; 79(2):800-11.
18. Russo J J, Bohenzky R A, Chien M C, Chen J, Yan M, Maddalena D, et al. Nucleotide sequence of the Kaposi sarcoma-associated herpesvirus (HHV8). Proceedings of the National Academy of Sciences of the United States of America. 1996; 93(25):14862-7.
19. Chandran B. Early events in Kaposi's sarcoma-associated herpesvirus infection of target cells. Journal of virology. 2010; 84(5):2188-99.
20. Akula S M, Pramod N P, Wang F-Z, Chandran B. Human herpesvirus 8 envelope-associated glycoprotein B interacts with heparan sulfate-like moieties. Virology. 2001, 284(2):235-49.
21. Akula S M, Pramod N P, Wang F Z, Chandran B. Human herpesvirus 8 envelope-associated glycoprotein B interacts with heparan sulfate-like moieties. Virology. 2001, 284(2):235-49.
22. Akula S M, Pramod N P, Wang F Z, Chandran B. Integrin alpha3beta1 (CD 49c/29) is a cellular receptor for Kaposi's sarcoma-associated herpesvirus (KSHV/HHV-8) entry into the target cells. Cell. 2002; 108(3):407-19.
23. Chakraborty S, Veettil M V, Bottero V, Chandran B. Kaposi's sarcoma-associated herpesvirus interacts with EphrinA2 receptor to amplify signaling essential for productive infection. Proceedings of the National Academy of Sciences of the United States of America. 2012,109 (19):E1163-72.
24. Veettil M V, Bandyopadhyay C, Dutta D, Chandran B. Interaction of KSHV with host cell surface receptors and cell entry. Viruses. 2014; 6(10):4024-46.
25. Hahn A S, Kaufmann J K, Wies E, Naschberger E, Panteleev-Ivlev J, Schmidt K, et al. The ephrin receptor tyrosine kinase A2 is a cellular receptor for Kaposi's sarcoma-associated herpesvirus. Nature medicine. 2012; 18(6):961-6.
26. Spiller O B, Mark L, Blue C E, Proctor D G, Aitken J A, Blom A M, et al. Dissecting the regions of virion-associated Kaposi's sarcoma-associated herpesvirus complement control protein required for complement regulation and cell binding. Journal of virology. 2006; 80(8):4068-78.
27. Spiller O B, Robinson M, O'Donnell E, Milligan S, Morgan B P, Davison A J, et al. Complement regulation by Kaposi's sarcoma-associated herpesvirus ORF4 protein. Journal of virology. 2003; 77(1):592-9.
28. Koyano S, Mar E C, Stamey F R, Inoue N. Glycoproteins M and N of human herpesvirus 8 form a complex and inhibit cell fusion. The Journal of general virology. 2003; 84(Pt 6):1485-91.
29. Chang Y, Cesarman E, Pessin M S, Lee F, Culpepper J, Knowles D M, et al. Identification of herpesvirus-like DNA sequences in AIDS-associated Kaposi's sarcoma. Science. 1994,266(5192):1865-9.
30. Barasa A, Ye P, Phelps M, Ganapathiram A, Tison T, Ogembo J G. BALB/c mice immunized with a combination of virus-like particles incorporating Kaposi sarcomaassociated herpesvirus (KSHV) envelope glycoproteins gpK8.1, gB, and gH/gL induced comparable serum neutralizing antibody activity to UV-inactivated KSHV Oncotarget. 2017; 8(21):34481-97.
31. Khodai T, Chappell D, Christy C, Cockle P, Eyles J, Hammond D, et al. Single and Combination Herpes Simplex Virus Type 2 Glycoprotein Vaccines Adjuvanted with CpG Oligodeoxynucleotides or Monophosphoryl Lipid A Exhibit Differential Immunity That Is Not Correlated to Protection in Animal Models. Clinical and Vaccine Immunology: CVI. 2011; 18(10):1702-9.
32. Wussow F, Chiuppesi F, Martinez J, Campo J, Johnson E, Flechsig C, et al. Human cytomegalovirus vaccine based on the envelope gH/gL pentamer complex. PLoS Pathog. 2014; 10(11):e1004524.
33. Fouts A E, Chan P, Stephan J P, Vandlen R, Feierbach B. Antibodies against the gH/gL/UL128/UL130/UL131

34. Genini E, Percivalle E, Sarasini A, Revello M G, Baldanti F, Gerna G. Serum antibody response to the gH/gL/pUL128-131 five-protein complex of human cytomegalovirus (HCMV) in primary and reactivated HCMV infections. J Clin Virol. 2011, 52(2):113-8.
35. Jinjong MaG, D. Generation of a doxycycline-inducible KSHV producer cell line of endothelial origin: maintenance of tight latency with efficient reactivation upon induction. Journal of Virological Methods. 2011,174(1): 12-21.
36. Totonchy J, Osborn J M, Chadburn A, Nabiee R, Argueta L, Mikita G, et al. KSHV induces immunoglobulin rearrangements in mature B lymphocytes. PLoS Pathog. 2018; 14(4):e1006967.
37. Myoung J, Ganem D. Generation of a doxycycline-inducible KSHV producer cell line of endothelial origin: maintenance of tight latency with efficient reactivation upon induction. Journal of virological methods. 2011,174 (1-2):12-21.
38. Zhu L, Puri V, Chandran B. Characterization of human herpesvirus-8 K8.1A/B glycoproteins by monoclonal antibodies. Virology. 1999,262(1):237-49.
39. Wang X J, Bai Y D, Zhang G Z, Zhao J X, Wang M, Gao G F. Structure and function study of paramyxovirus fusion protein heptad repeat peptides. Arch Biochem Biophys. 2005; 436(2):316-22.
40. Morrison T G. Structure and function of a paramyxovirus fusion protein. Biochim Biophys Acta. 2003; 1614(1): 73-84.
41. Kim J H, Lee S R, Li L H, Park H J, Park J H, Lee K Y, et al. High cleavage efficiency of a 2A peptide derived from porcine teschovirus-1 in human cell lines, zebrafish and mice. PLoS One. 2011; 6(4):e18556.
42. Pantua H D, McGinnes L W, Peeples M E, Morrison T G. Requirements for the assembly and release of Newcastle disease virus-like particles. J Virol. 2006; 80(22):11062-73.
43. Gibson D G, Young L, Chuang R Y, Venter J C, Hutchison C A, 3rd, Smith H O. Enzymatic assembly of DNA molecules up to several hundred kilobases. Nat Methods. 2009; 6(5):343-5.
44. Broering T J, Garrity K A, Boatright N K, Sloan S E, Sandor F, Thomas W D, et al. Identification and characterization of broadly neutralizing human monoclonal antibodies directed against the E2 envelope glycoprotein of hepatitis C virus. Journal of virology. 2009; 83(23): 12473-82.
45. Labo N, Miley W, Marshall V, Gillette W, Esposito D, Bess M, et al. Heterogeneity and breadth of host antibody response to KSHV infection demonstrated by systematic analysis of the KSHV proteome. PLoS Pathog. 2014; 10(3):e1004046.
46. Kumar P, Kuwa N Y, Minhas V, Marimo C, Shea D M, Kankasa C, et al. Higher levels of neutralizing antibodies against KSHV in K S patients compared to asymptomatic individuals from Zambia. PLoS One. 2013; 8(8):e71254.
47. Perez E M, Foley J, Tison T, Silva R, Ogembo J G. Novel Epstein-Barr virus-like particles incorporating gH/gL-EBNA1 or gB-LMP2 induce high neutralizing antibody titers and EBV-specific T-cell responses in immunized mice. Oncotarget. 2016.
48. Nicol S M, Sabbah S, Brulois K F, Jung J U, Bell A I, Hislop A D. Primary B lymphocytes infected with KSHV can be expanded in vitro and are recognized by LANA-specific CD4+ T cells. Journal of virology. 2016:JVI. 02377-15.
49. Sabbah S, Jagne Y J, Zuo J, de Silva T, Ahasan M M, Brander C, et al. T-cell immunity to Kaposi sarcoma-associated herpesvirus: recognition of primary effusion lymphoma by LANA-specific CD4+ T cells. Blood. 2012; 119(9):2083-92.
50. Mayr A, Hochstein-Mintzel V, Stickl H, Infection 3(1): 6-14 (1975).
51. Lane J M, Mass vaccination and surveillance/containment in the eradication of smallpox, Curr. Top. Microbio. Immunol. 2006, 304: 17-29.
52. Goepfert P A, et al., Phase 1 safety and immunogenicity testing of DNA and recombinant modified vaccinia Ankara vaccines expressing HIV-1 virus-like particles, J. Infect. Dis. 2011, 203(5): 610-619.
53. Goepfert P A, et al., Specificity and 6-month durability of immune responses induced by DNA and recombinant modified vaccinia Ankara vaccines expressing HIV-1 virus-like particles, J. Infect. Dis. 2014, 210(1): 99-110.
54. Carroll M W, Moss B, Host range and cytopathogenicity of the highly attenuated MVA strain of vaccinia virus: propagation and generation of recombinant viruses in a nonhuman mammalian cell line, Virology 1997, 238(2): 198-211.
55. Chiuppesi et al., Multiantigenic Modified Vaccinia Virus Ankara Vaccine Vectors to Elicit Potent Humoral and Cellular Immune Responses against Human Cytomegalovirus in Mice, J. Virology 2018, 92(19) e01012-18.
56. Tischer et al., En passant mutagenesis: a two step markerless red recombination system, Methods Mol Biol 2010, 634: 421-430.

What is claimed is:

1. A multivalent Kaposi sarcoma-associated herpesvirus-like particle (KSHV-LP) comprising four KSHV glycoproteins or immunogenic fragments thereof, wherein the four KSHV glycoproteins incorporated by the multivalent KSHV-LP comprise (i) a gpK8.1 ectodomain fused to an Newcastle disease virus (NDV) structural protein sequence, (ii) a gB ectodomain fused to an NDV structural protein sequence, (iii) a gH ectodomain fused to an NDV structural protein sequence, and (iv) a full-length gL glycoprotein.

2. The KSHV-LP of claim 1, further comprising one or more T cell antigens.

3. The KSHV-LP of claim 2, wherein the T cell antigen includes LANA1 or an immunogenic fragment thereof.

4. The KSHV-LP of claim 1, wherein at least one of the NDV structural proteins comprise fusion (F), matrix (M), or nucleocapsid (NP).

5. A vaccine composition or a pharmaceutical composition comprising a therapeutically effective amount of the KSHV-LP of claim 1.

6. A vaccine composition or a pharmaceutical composition comprising a therapeutically effective amount of a multivalent KSHV-LP comprising four KSHV glycoproteins and one or more T cell antigens, wherein the four KSHV glycoproteins incorporated by the multivalent KSHV-LP comprise (i) a gpK8.1 ectodomain fused to an NDV structural protein sequence, (ii) a gB ectodomain fused to an NDV structural protein sequence, (iii) a gH ectodomain fused to an NDV structural protein sequence, and (iv) a full-length gL glycoprotein.

7. The vaccine composition or pharmaceutical composition of claim 6, wherein the one or more T cell antigens include LANA1 or a fragment thereof.

8. The vaccine composition or pharmaceutical composition of claim 6, wherein at least one of the NDV structural proteins comprise fusion (F), matrix (M), or nucleocapsid (NP).

9. The vaccine composition or the pharmaceutical composition of claim 5, further comprising one or more adjuvants or one or more pharmaceutically acceptable carriers.

10. The vaccine composition or the pharmaceutical composition of claim 6, further comprising one or more adjuvants or one or more pharmaceutically acceptable carriers.

11. A method of preventing a disease associated with KSHV infection or treating a KSHV infection or a condition associated with a KSHV infection comprising administering to a subject in need thereof a therapeutically effective amount of the KSHV-LP of claim 1.

12. A method of preventing a disease associated with KSHV infection or treating a KSHV infection or a condition associated with a KSHV infection comprising administering to a subject in need thereof the vaccine composition or pharmaceutical composition of claim 6.

13. An immunization regimen comprising administering to a subject in need thereof one or more doses of a therapeutically effective amount of the KSHV-LP of claim 1.

14. An immunization regimen comprising administering to a subject in need thereof one or more doses of the vaccine composition or pharmaceutical composition of claim 6.

15. An expression system for co-expressing four KSHV envelope glycoproteins including a multivalent vector inserted with four nucleic acid sequences that encode four KSHV envelope glycoproteins, linked by one or more linking sequences, such that the four KSHV envelope glycoproteins can be co-expressed simultaneously, self-cleaved and/or self-processed to assemble into one or more glycoprotein complexes, wherein the four KSHV envelope glycoproteins incorporated by the multivalent KSHV-LP comprise (i) a gpK8.1 ectodomain fused to an Newcastle disease virus (NDV) structural protein sequence, (ii) a gB ectodomain fused to an NDV structural protein sequence, (iii) a gH ectodomain fused to an NDV structural protein sequence, and (iv) a full-length gL glycoprotein.

16. A method of preventing a disease associated with KSHV infection or neutralizing KSHV infection in vitro comprising contacting a cell line permissive to KSHV infection with the KSHV-LP of claim 1 such that a neutralizing antibody is produced.

\* \* \* \* \*